United States Patent [19]
Vermeer et al.

[11] Patent Number: 5,631,389
[45] Date of Patent: May 20, 1997

[54] NONIONIC GLYCASUCCINIMIDE SURFACTANTS AND A PROCESS FOR THEIR MANUFACTURE

[75] Inventors: Robert Vermeer, Nutley, N.J.; Van Au, New City, N.Y.; Bijan Harichian, South Orange, N.J.

[73] Assignee: Lever Brothers Company, Division of Conopco, Inc., New York, N.Y.

[21] Appl. No.: 640,394

[22] Filed: Apr. 30, 1996

Related U.S. Application Data

[62] Division of Ser. No. 410,178, Mar. 24, 1995, Pat. No. 5,541,341.

[51] Int. Cl.$^6$ .................. C07D 307/20; C07D 309/10
[52] U.S. Cl. .................. 549/417; 549/478; 560/170; 562/512; 562/553; 562/567; 562/579; 562/587; 564/152; 564/193; 564/197; 564/198; 564/199; 564/201; 564/215

[58] Field of Search .................. 549/417, 478; 560/170; 562/512, 553, 567, 579, 587; 564/152, 193, 197, 198, 199, 201, 215

[56] References Cited

U.S. PATENT DOCUMENTS

| | | | |
|---|---|---|---|
| 2,613,206 | 10/1952 | Caldwell | 260/233.5 |
| 2,661,349 | 12/1953 | Caldwell | 260/224 |
| 2,868,781 | 1/1959 | Gaertner et al. | 260/234 |
| 2,903,382 | 9/1959 | Berls | 117/143 |
| 2,973,353 | 2/1961 | Gaertner | 260/234 |
| 3,053,830 | 9/1962 | Gaertner | 260/234 |
| 3,219,657 | 11/1965 | Gaertner | 260/234 |

*Primary Examiner*—Joseph McKane
*Attorney, Agent, or Firm*—Ronald A. Koatz

[57] ABSTRACT

The present invention relates to a new class of carbohydrate based nonionic surfactant, i.e., alkyl and alkenyl glycasuccinimide, and a process for their manufacture.

2 Claims, No Drawings

NONIONIC GLYCASUCCINIMIDE SURFACTANTS AND A PROCESS FOR THEIR MANUFACTURE

This is a divisional application of Ser. No. 08/410,178, filed Mar. 24, 1995, now U.S. Pat. No. 5,541,341.

TECHNICAL FIELD

The present invention is related to a new class of carbohydrate based nonionic surfactant, specifically alkyl- and alkenyl glycasuccinimide compounds and a process for their manufacture.

BACKGROUND OF THE INVENTION

The demand for mild, biodegradable, environmentally friendly surfactants has been steadily rising. In general, most surfactants are based on, or derived from petrochemicals. Since these materials can have handling, storage and environmental hazards associated with them, it would be most desirable to use surfactants which are instead derived from agriculturally grown materials, such as carbohydrates. These naturally occurring compounds represent a source of renewable raw materials that are readily available, inexpensive, biodegradable, aquatically favorable and optically pure.

A new class of carbohydrate based surfactant has now been found, specifically nonionic alkyl- and alkenyl glycasuccinimide surfactants and a process for their manufacture. These compounds were found to have surfactant properties equal to, or better than, other well known nonionic surfactants based on petrochemicals, thereby indicating that they are viable sound alternatives to traditional petrochemical surfactants.

BACKGROUND ART

An alkyl- or alkenyl glycasuccinimide is defined as an alkyl- or alkenyl imide of an 1-amino-1-deoxyalditol, 1-amino-1,6-dideoxyalditol or 2-amino-2-deoxyketitol, which in turn, is defined as a sugar substance in which the pseudoaldehyde or pseudoketose group, generally found at the $C_1$ or $C_2$ position of the sugar, has been reduced to an amino group through a reductive amination reaction with ammonia and hydrogen in the presence of a metal catalyst such as nickel. The reaction is typically done in water or organic solvent, but is usually done in a mixture of both. Methods of preparing such glycamines are well known in the art and are described in the J. Chem. Soc. 1682, (1922) to Ling et al.; J. Amer. Chem. Soc. 62, 3315, (1940) to Wayne et al., 72, 5416, (1950) to Holly et al., 79, 3541, (1957) to Kagan et al.; Methods in Carbohydr. Chem. 2, 79, (1964) to Long et al.: U.S. Pat. Nos. 2,016,962 to Flint et al., 2,621,175 to Holly et al.; and EP Application No. 0,536,939 to Beck all of which are incorporated herein by reference.

An alkyl- or alkenyl glycasuccinlmide can also be defined as an alkyl- or alkenyl imide of a Z-amino-Z-deoxyalditol (hydrogenated aldosamine or ketosamine), wherein Z is from about 2 to about 8, which in turn, is defined as a sugar substance in which the pseudoaldehyde or pseudoketose group, generally found at the $C_1$ or $C_2$ position of the sugar, has been reduced to a hydroxyl group with hydrogen in the presence of a metal catalyst such as nickel or platinum or a metal reducing agent such as sodium borohydride. The reaction is typically done in water. Methods of preparing such glycamines are well known in the art and are described in the J. Biol. Chem. 120, 577, (1937) to Levene et al.: Helv. Chim. Acta. 20, 627, (1937) to Karrer et al.; Chem. Ber. 102, 459, (1969) to Paulsen et al.; and U.S. Pat. No. 4,307,072 to Smith all of which are incorporated herein by reference.

An alkyl- or alkenyl glycasuccinimide can be further defined as an alkyl- or alkenyl imide of a Z-amino-Z-deoxyaldose, Z-amino-Z-deoxy-ketose, Z-amino-Z-deoxyglycoside, wherein Z is from about 1 to about 8. Methods of preparing or isolating such glycamines are well known in the art and are described in Adv. Carbohydr. Chem. 7, 247, (1957) to Foster et al., 13, 189, (1958) to Jeanloz,; Methods in Carbohydr. Chem. 1, 228, (1962) to Stacey et al.; Chem. Ber. 103, 1599, (1970) to Paulsen et al.; Can. J. Chem. 46, 1586, (1968) to Sowa et al.; J. Am. Chem. Soc. 81, 3716, (1959) to Wolfrom et al.; Helv. Chim. Acta 46, 282, (1963) to Hardegger et al., 40, 342, (1957) to Druey et al.; Ann. 148, 600, (1956) to Kuhn et al,; and J. Org. Chem. 26, 603, (1961) to Zaugg all of which are incorporated herein by reference.

A glycasuccinimide may be based on carbohydrates comprising one saccharide unit (e.g., ribosuccinimides, glucosuccinimides, 2-deoxy-2-aminosorbitolsuccinimides, glucoheptosuccinimides or fructosuccinimides), two saccharide units (e.g., lactosuccinimides, maltosuccinimides or cellobiosuccinimides), three saccharide units (e.g., maltotriosuccinimides or cellotriosuccinimides) or they may be based on compounds comprising more than three saccharide units (e.g., maltoheptosuccinimides). It should be noted that any carbohydrate can be used as long as the sugar has an amino group or a pseudoaldehyde or pseudoketose group available for reduction to an amino group.

While certain allyl- and alkenyl sugar succinate esters are known in the art, there is no teaching or suggestion of alkyl- and alkenyl sugar succinate imides (glycasuccinimides) of the present invention as surface-active agents.

U.S. Pat. No. 2,613,206 to Caldwell teaches the manufacture and use of alkyl- and alkenyl starch succinate esters of the formula:

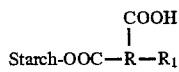

wherein:

R represents a $CH_2CH$ (dimethylene) or $CH_2CH_2CH$ (trimethylene) group; and $R_1$ represents an alkyl, alkenyl, aralkyl or aralkenyl group having 1 to 18 carbon atoms.

The alkyl- and alkenyl starch succinate esters are prepared by the reaction of starch with alkyl- or alkenyl succinic or glutaric arthydride In the presence of a base catalyst. The reaction is preferably performed in water, but optionally may be performed in a near dry state (5% to 20% water) or in an organic solvent such as benzol. These compounds are anionic in nature and are said to be useful as free flowing agents for offset dry spray printing applications, as carriers for insecticide powders, as delustering agents for cellulase acetate rayons or lacquers, as rubber finishing aids and as water repellents for textile sizing and finishing. There is clearly no teaching or suggestion of the alkyl- and alkenyl glycasuccinimide compounds of the present invention as surface-active agents. Furthermore, the alkyl- and alkenyl glycasuccinimide compounds of the present invention are nonionic in nature and are completely different structurally.

U.S. Pat. No. 2,661,349 to Caldwell et al. teaches the manufacture and use of alkyl- and alkenyl polysaccharide succinate esters of the formula:

wherein:
polysaccharide represents starch, cellulose, methylcellulose or dextrin;

$R_2$ represents a $CH_2CH$ (dimethylene) or $CH_2CH_2CH$ (trimethylene) group; and $R_3$ represents an alkyl, alkenyl, or aralkyl or an aralkenyl group having 5 to 18 carbon atoms.

The alkyl- and alkenyl polysaccharide succinate esters are prepared by the reaction of a polysaccharide with alkyl or alkenyl succinic or glutaric anhydride in the presence of a base catalyst. The reaction is preferably performed in water, but optionally may be performed in the near dry state (5% to 20% water) or in an organic solvent such as benzol, pyridine or toluene. These compounds are anionic in nature and are said to be useful as emulsifying and thickening agents. There is clearly no teaching or suggestion of the alkyl- and alkenyl glycasuccinimide compounds of the present invention as surface-active agents. Furthermore, the alkyl- and alkenyl glycasuccinimide compounds of the present invention are nonionic in nature and are completely different structurally.

U.S. Pat. No. 2,868,781 and J. Am. Oil Chemists Soc., 38, 410 (1961) to Gaertner et al. teaches the manufacture and use of alkyl- and alkenyl disugar succinate esters of the formula:

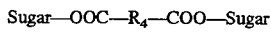

wherein:
sugar represents glucose, fructose, methyl α-D-glucoside, sorbitol, sucrose, methyl γ-glucoside, L-sorbose, maltose, lactose, L-xylulose, γ-methyl fructoside, D-mannitol, D-arabitol, xylitol, starch or dextrin and;

$R_4$ represents an alkyl-$CHCH_2$, alkenyl-$CHCH_2$ or alkoxy $CHCH_2$ group having 5 to 20 carbon atoms.

The alkyl- and alkenyl disugar succinate esters are prepared by the reaction of excess sugar with alkyl- or alkenyl succinic acid or anhydride in the presence of a base catalyst and solvent such as dimethylformamide, pyridine or dimethylsulfoxide. These compounds are said to be useful as surface-active agents. There is clearly no teaching or suggestion of the alkyl- and alkenyl glycasuccinimide compounds of the present invention which are completely different structurally.

U.S. Pat. No. 2,903,382 to Beris teaches a method of water-proofing cellulosic fabrics using alkenyl succinic acid or anhydride to produce alkenyl cellulose succinate esters of the formulas:

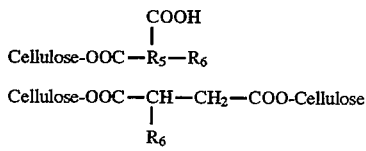

wherein:
cellulose represents cellulosic textiles such as cotton, mercerized cotton or linen;

$R_5$ represents a $CH_2CH$ group; and $R_6$ represents an alkenyl group having 19 to 35 carbon atoms.

The alkenyl cellulose succinate esters are prepared by impregnating cellulose fibers with alkenyl succinic acid or anhydride in the presence of base catalyst and water or solvent such as isopropanol, benzene, toluene, chloroform and carbon tetrachloride. There is clearly no teaching or suggestion of the alkyl- and alkenyl glycasuccinimide compounds of the present invention which are useful as surface-active agents.

U.S. Pat. Nos. 2,973,353 and 3,053,830 to Gaertner, teaches the manufacture and use of alkyl- and alkenyl monosugar succinate esters of the formula:

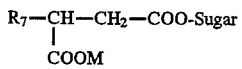

wherein:
sugar represents glucose, fructose, methyl α-D-glucoside, sorbitol, sucrose, maltose, lactose, L-sorbose, L-xylulose, β-methyl D-glucoside, β-methyl fructoside, γ-methyl L-fructoside or other glycosides;

$R_7$ represents an alkyl or alkenyl group having 6 to 20 carbon atoms; and M represents hydrogen or a salt forming cation.

The alkyl- and alkenyl monosugar succinate esters are prepared by the reaction of sugar with alkyl- or alkenyl succinic acid or anhydride in the presence of a base catalyst. The reaction is usually performed in the presence of an organic solvent such as dimethylformamide, diethylformamide, dipropylformamide, dimethylacetamide, diethylacetamide, dimethylpropionamide, dimethylsulfoxide, dimethylsulfoxide or pyridine. These compounds are said to be useful as emulsifying agents, wetting agents and foaming agents. There is clearly no teaching or suggestion of the alkyl- and alkenyl glycasuccinimide compounds of the present invention which are useful as surface-active agents. Also, the alkyl- and alkenyl monosugar succinate esters of U.S. Pat. Nos. 2,973,353 and 3,053,830 are anionic in nature where as the compounds of this invention are nonionic in nature.

U.S. Pat. No. 3,219,657 to Gaertner, teaches the manufacture and use of alkyl- and alkenyl saccharide polydicarboxylate half-esters of the formula:

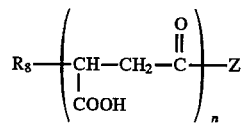

wherein:
Z represents glucose, fructose, methyl α-D-glucoside, sorbitol,

β-methyl D-glucoside, β-methyl fructoside, γ-methyl D-glucoside,

γ-methyl L-fructoside, D-mannitol, D-arabitol, xylitol, sucrose, maltose or lactose;

$R_8$ is an alkyl or alkenyl group having 6 to 20 or more carbons: and n is at least 2 up to 8.

The alkyl- and alkenyl saccharide polydicarboxylate esters are prepared by the reaction of sugar with excess alkyl- or alkenyl succinic anhydride in the presence of base catalyst and solvent such as dimethylformamide, pyridine or dimethylsulfoxide. The reaction may be preformed in a melt, however, browning reactions or decomposition of the sugar substrate often occurs, yielding compounds that are dark In color. There is clearly no teaching or suggestion of the alkyl- and alkenyl glycasuccinimide compounds of the present invention which are isolated in high yield as white crystalline solids.

JP 4,288,092 to Nakajima teaches a process for the manufacture of alkenyl sugar succinate esters which are useful as emulsifiers, detergents, protective colloids and cosmetic bases for toiletry articles. Useful sugar substrates include glucose, mannose, allose, altrose, talose, galaclose, idose, gulose, fructose, tagarose, ribose, arabinose, xylose, lyxose, sorbose, ribulose, xylulose, psicose, rhamnose, sucrose, maltodextrin, cyclodextrin, isomaltodextrin, celloоligosaccharide, galactooligosaccharide, mannooligosaccharide, hydrolyzed starch, caramelized sugar, glucosamine, galactosamine, condurosamine, mannosamine, gulosamine, kanosamine, glucuronic acid, guluronic acid, galacturonic acid, mannuronic acid, glycerol, erythritol, ribitol, arabinitol, mannitol, sorbitol, glucitol, dulcitol and starch syrups. Although JP 4,288,092 describes the use of certain glycamines as useful starting materials (substrates), this patent fails to teach or contemplate the alkyl- and alkenyl glycasuccinimides of the present invention which are structurally different. Also, the process in JP 4,288,092 requires the use of water and organic solvents such as alcohol or acetone, and produces surfactants that are anionic in nature not nonionic in nature as described In this disclosure.

Lastly, it should be noted that all the above processes require costly organic solvents, some of which have handling, storage and environmental hazards associated with them. The process of this invention can also use organic solvents, however, it is not required making this process more viable and commercially feasible. Also, as seen in comparative Example 1, the compounds prepared by previous methods, are generally isolated as thick colored syrups which are difficult to handle and isolate. The alkyl- and alkenyl glycasuccinimide compounds of this invention are isolated as crystalline solids in good yield, high purity, and desirable color.

Thus, the ability to find a naturally derived, environmentally friendly, biodegradable, solid sugar based nonionic surfactant and a viable, cost-effective, commercially feasible method for their manufacture is a significant achievement.

Accordingly, it is an objective of the present invention to provide novel nonionic alkyl- and alkenyl glycasuccinimide compounds as surface-active agents.

It is another object of the present invention to provide naturally derived, cost-effective nonionic alkyl- and alkenyl glycasuccinimide surfactants.

It is another object of the present invention to provide nonionic alkyl- and alkenyl glycasuccinimide surfactants that dissolve readily and foam well in water.

It is still another object of the present invention to provide nonionic alkyl- and alkenyl glycasuccinimide surfactants that have a low surface tension and a favorable critical micelle concentration in water.

It is still another object of the present invention to provide a viable, commercially feasible process for the manufacture of nonionic alkyl- and alkenyl glycasuccinimide surfactants.

It is a final object of the present invention to prepare solid nonionic alkyl- and alkenyl glycasuccinimide surfactants in good yield, high purity, and desirable color without hydroxyl group protection, oligomerization or polymerization. These and other objects will become readily apparent from the detailed description which follows.

SUMMARY OF THE INVENTION

In one embodiment of the invention, the invention relates to a new class of carbohydrate based nonionic surfactant, specifically novel nonionic alkyl- and alkenyl glycasuccinimide surfactants.

In another embodiment of the invention, the invention relates to a new and improved process for preparing such surfactants. The process is an improvement over the art known processes for the preparation of alkyl- and alkenyl sugar succinate esters, wherein the improvement comprises reacting an alkyl- or alkenyl succinic acid ester or anhydride directly (without a solvent) with a glycamine in the presence of a base catalyst. This embodiment of the invention is particularly directed to preparing solid alkyl- and alkenyl glycasuccinimide compounds in good yield, high purity and desirable color without hydroxyl group protection, oligomerization or polymerization and so the process of manufacture is commercially feasible and economically viable.

The alkyl- and alkenyl glycasuccinimide compounds of the invention have surfactant properties equal to, or better than, other well known nonionic surfactants based on petrochemicals, thereby indicating that they are viable sound alternatives to traditional petrochemical surfactants.

DETAILED DESCRIPTION OF THE INVENTION

The present invention relates to a new class of environmentally friendly "green" nonionic carbohydrate based surfactant. In particular, one embodiment of the invention describes novel nonionic alkyl- and alkenyl glycasuccinimide surfactants.

In another embodiment of the invention, a new and improved process for the manufacture of alkyl- and alkenyl glycasuccinimide surfactants is described.

In general, the nonionic alkyl- and alkenyl glycasuccinimide surfactants are of the formula:

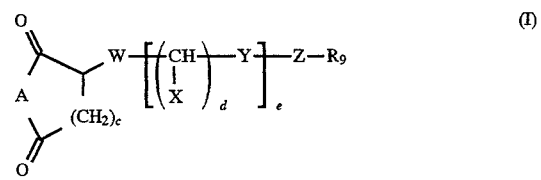

wherein:

A represents the following structures which are attached to the succinate ring via the nitrogen (N) atom;

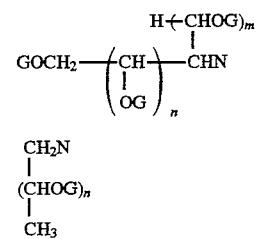

-continued

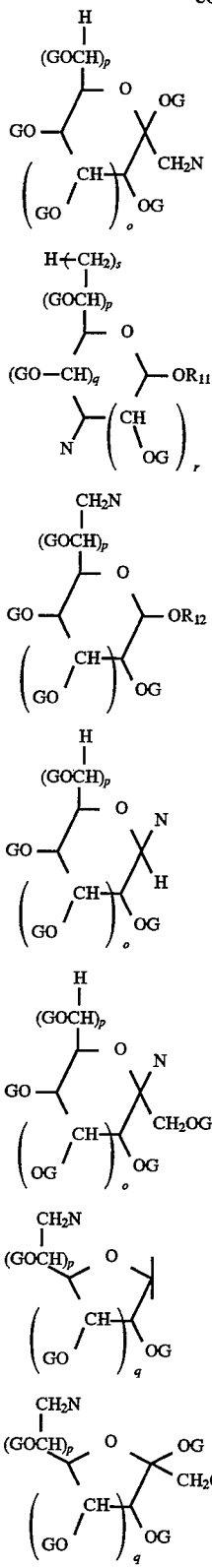

G is hydrogen (H), a SO$_3$M, PO$_3$M$_2$, (CH$_2$CH$_2$O)$_a$H or (CH$_2$CHCH$_3$O)$_b$H group, a mono-, di-, oligo- or polysaccharide or mixtures thereof;

M is hydrogen (H), an alkali metal, alkaline earth metal, ammonium, alkyl substituted ammonium or mono-, di-, trialkanolammonium group having about 1 to about 5 carbon atoms;

W is a CH$_2$ group, oxygen atom (O) or mixtures thereof;

X is hydrogen (H), an alkyl group having about 1 to about 4 carbon atoms or mixtures thereof;

Y is a NR$_{10}$, +N(R$_{10}$)$_2$, O, S, SO, SO$_2$, COO, OOC, CONR$_{10}$, NR$_{10}$CO group or mixtures thereof;

Z is a CH=CH, CH$_2$CH$_2$ group or mixtures thereof;

R$_9$ is a straight or branched chain saturated or unsaturated hydrocarbon which may be unsubstituted or substituted with an aromatic, cycloaliphatic or mixed aromatic radical having about 1 to about 31 carbon atoms;

R$_{10}$ is hydrogen (H), a hydroxylalkyl group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 8 carbon atoms;

R$_{11}$ is hydrogen (H), or an arkyl, alkenyl or hydroxyalkyl group having about 1 to about 6 carbon atoms;

R$_{12}$ is hydrogen (H), or an alkyl, alkenyl or hydroxyalkyl group having about 1 to about 6 carbon atoms;

a=0–35;
b=0–35;
c=1–3;
d=1–5;
e=0–35;
m=0–8;
n=1–6;
o=0–2;
p=0–4;
q=0–3;
r=0–3;
and s=0–1.

preferably:

A represents the following structures which are attached to the succinate ring via the nitrogen (N) atom;

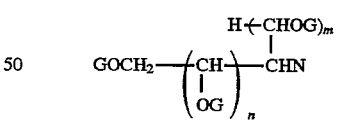

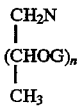

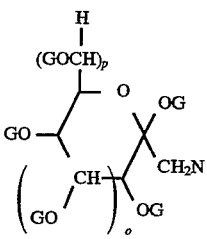

-continued $$\begin{array}{c} H\!-\!(CH_2)_s \\ | \\ (GOCH)_p \\ | \\ (GO\!-\!CH)_q \end{array}\!\!\!\!\begin{array}{c} O \\ \diagup \\ \diagdown \end{array}\!\!\!\!OR_{11}$$

$$N\!\!\left(\begin{array}{c} CH \\ | \\ OG \end{array}\right)_r$$

$$\begin{array}{c} CH_2N \\ | \\ (GOCH)_p \\ | \\ GO \end{array}\!\!\!\!\begin{array}{c} O \\ \diagup \\ \diagdown \end{array}\!\!\!\!OR_{12}$$

$$\left(\begin{array}{c} CH \\ GO \end{array}\!\!\!\!\begin{array}{c} \\ OG \end{array}\right)$$

$$\begin{array}{c} H \\ | \\ (GOCH)_p \\ | \\ GO \end{array}\!\!\!\!\begin{array}{c} O \\ \diagup \\ \diagdown \end{array}\!\!\!\!\begin{array}{c} N \\ | \\ H \end{array}$$

$$\left(\begin{array}{c} CH \\ GO \end{array}\!\!\!\!\begin{array}{c} \\ OG \end{array}\right)_o$$

$$\begin{array}{c} H \\ | \\ (GOCH)_p \\ | \\ GO \end{array}\!\!\!\!\begin{array}{c} O \\ \diagup \\ \diagdown \end{array}\!\!\!\!\begin{array}{c} N \\ | \\ CH_2OG \end{array}$$

$$\left(\begin{array}{c} CH \\ OG \end{array}\!\!\!\!\begin{array}{c} \\ OG \end{array}\right)_o$$

$$\begin{array}{c} CH_2N \\ | \\ (GOCH)_p \\ | \end{array}\!\!\!\!\begin{array}{c} O \\ \diagup \\ \diagdown \end{array}$$

$$\left(\begin{array}{c} CH \\ GO \end{array}\!\!\!\!\begin{array}{c} \\ OG \end{array}\right)_q$$

$$\begin{array}{c} CH_2N \\ | \\ (GOCH)_p \\ | \end{array}\!\!\!\!\begin{array}{c} O \\ \diagup \\ \diagdown \end{array}\!\!\!\!\begin{array}{c} OG \\ CH_2OG \end{array}$$

$$\left(\begin{array}{c} CH \\ GO \end{array}\!\!\!\!\begin{array}{c} \\ OG \end{array}\right)_q$$

G is hydrogen (H), a $(CH_2CH_2O)_aH$ or $(CH_2CHCH_3O)_bH$ group, a mono- di- or oligosaccharide or mixtures thereoff W is a $CH_2$ group, oxygen atom (O) or mixtures thereof X is hydrogen (H), an alkyl group having about 1 to about 3 carbon atoms or mixtures thereoff Y is a $NR_{10}$, $+N(R_{10})_2$, O, COO, OOC group or mixtures thereof;

Z is a CH=CH, $CH_2CH_2$ group or mixtures thereof;

$R_9$ is a straight or branched chain saturated or unsaturated hydro-carbon which may be unsubstituted or substituted with an aromatic, cycloaliphatic or mixed aromatic radical having about 2 to about 25 carbon atoms;

$R_{10}$ is hydrogen (H), a hydroxylalkyl group having about 1 to about 4 carbon atoms, a straight or branched chain, saturated or unsaturated hydrocarbon radical having about 1 to about 5 carbon atoms;

$R_{11}$ is hydrogen (H), or an alkyl, alkenyl or hydroxyalkyl group having about 1 to about 5 carbon atoms;

$R_{12}$ is hydrogen (H), or an alkyl, alkenyl or hydroxyalkyl group having about 1 to about 5 carbon atoms;

a=0–25;
b=0–25;
c=1–3;
d=1–4;
e=0–25;
m=0–7;
n=1–5;
o=0–2;
p=0–3;
q=0–2;
r=0–2;
and s=0–1.

More preferably:

A represents the following structures which are attached to the succinate ring via the nitrogen (N) atom;

$$\begin{array}{c} H\!-\!(CHOG)_m \\ | \\ GOCH_2\!-\!\!\left(\!\!\begin{array}{c} CH \\ | \\ OG \end{array}\!\!\right)_n\!\!\!\!-CHN \end{array}$$

$$\begin{array}{c} CH_2N \\ | \\ (CHOG)_n \\ | \\ CH_3 \end{array}$$

$$\begin{array}{c} GO \end{array}\!\!\!\!\begin{array}{c} O \\ \diagup \\ \diagdown \end{array}\!\!\!\!OR_{12}$$

$$\left(\begin{array}{c} CH \\ GO \end{array}\!\!\!\!\begin{array}{c} \\ OG \end{array}\right)_o$$

$$\begin{array}{c} CH_2N \\ | \\ (GOCH)_p \end{array}\!\!\!\!\begin{array}{c} O \\ \diagup \\ \diagdown \end{array}$$

$$\left(\begin{array}{c} CH \\ GO \end{array}\!\!\!\!\begin{array}{c} \\ OG \end{array}\right)_q$$

G is hydrogen (H), a $(CH_2CH_2O)_aH$ or $(CH_2CHCH_3O)_bH$ group, a mono-saccharide or mixtures thereof;

X is hydrogen (H), an alkyl group having about 1 to about 2 carbon atoms or mixtures thereof;

Y is an oxygen atom (O) or a COO or OOC group or mixtures thereof;

Z is a CH=CH, $CH_2CH_2$, group or mixtures thereof:

$R_9$ is a straight or branched chain saturated hydrocarbon radical having about 3 to about 23 carbon atoms;

$R_{12}$ is hydrogen (H), or an alkyl, alkenyl or hydroxyalkyl group having about 1 to about 4 carbon atoms:

a=0–15;
b=0–15;
c=1–2;
d=1–4;
e=0–15;
m=0–5;

n=1–5;
o=0–1;
p=0–2;
and q=0–2.

A specific example of a monosaccharide alkyl glycasuccinimide compound of the invention is dodecyloxy D-glucosuccinimide having the formula:

wherein based on formula (I) above:

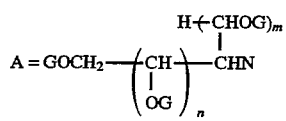

G=hydrogen (H);
$R_9=C_{10}H_{21}$;
W=oxygen (O);
Z=$CH_2CH_2$;
c=1;
e=0;
and n=4.

Another specific example of a monosaccharide alkyl glycasuccinimide compound of the invention is tetradecyloxytri(oxyethyl) D-glucosuccinimide, also known as tetradecyloxy(triethylene glycol) ether D-glucosuccinimide or as tetradecyloxy(trioxyethylene) D-glucosuccinimide having the formula:

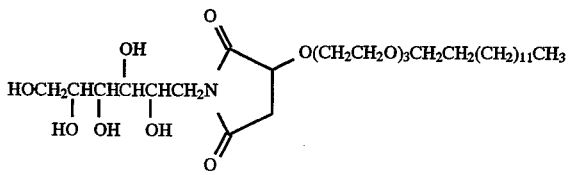

wherein based on formula (I) above:

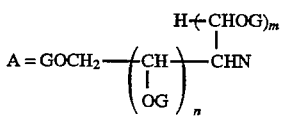

G=hydrogen (H);
$R_9=C_{12}H_{25}$;
W=oxygen (O);
X=hydrogen (H);
Y=oxygen (O);
Z=$CH_2CH_2$;
c=1;
d=2;
e=3;
m=0;
and n=4.

Yet another specific example of a monosaccharide alkyl glycasuccinimide compound of the invention is dodecyl D-glucosuccinimide tetraoxyethylene ether, also known as dodecyl D-glucosuccinimide tetraethylene glycol ether or more generally as polyoxyethylene (4) dodecyl D-glucosuccinimide having the formula:

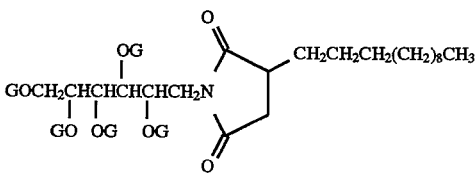

wherein based on formula (I) above:

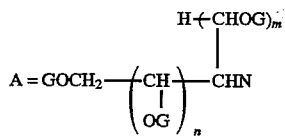

G=hydrogen (H) or $(CH_2CH_2O)_aH$ group;
$R_9 =C_9H_{19}$;
W=$CH_2$;
Z=$CH_2CH_2$;
a=can vary from about 1 to about 8 for a total average of 4;
c=1;
e=0;
m=0;
and n=4.

A specific example of a monosaccharide alkenyl glycasuccinimide compound of the invention is decenyl D-glucosuccinimide also known as decenyl 1-imino-1-deoxy D-glucitol succinate or decenyl 1-imino-1-deoxy D-sorbitol succinate having the formula:

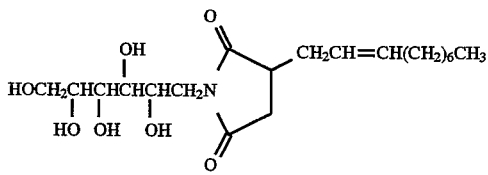

wherein based on formula (I) above:

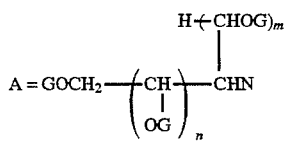

G=hydrogen (H);
R$_9$=C$_7$H$_{15}$;
W=CH$_2$;
Z=CH=CH;
c=1;
e=0;
m=0;
and n=4.

Another specific example of a monosaccharide alkenyl glycasuccinimide compound of the invention is dodecenyl L-rhamnosuccinimide also know as dodecenyl 1-imino-1,6-dideoxy L-rhamnitol succinate or dodecenyl 1-imino-1,6-dideoxy L-mannitol succinate having the formula:

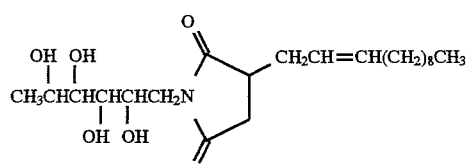

wherein based on formula (I) above:

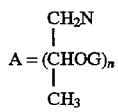

G=hydrogen (H);
R$_9$=C$_9$H$_{19}$;
W=CH$_2$;
Z=CH=CH;
c=1;
e=0;
and n=4.

A specific example of a cyclic monosaccharide alkenyl glycasuccinimide compound of the invention is decenyl D-sorbitansuccinimide having the formula:

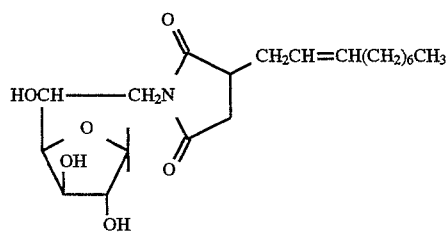

wherein based on formula (I) above:

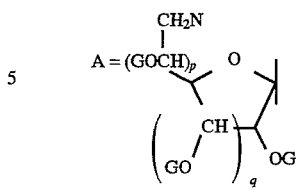

G=hydrogen (H);
R$_9$=C$_7$H$_{15}$;
W=CH$_2$;
Z=CH=CH;
c=1;
e=0;
p=1;
and q=1.

Another specific example of a cyclic monosaccharide alkenyl glycasuccinimide compound of the invention is dodecenyl 1-imino-1-deoxy D-fructopyranosyl succinate having the formula:

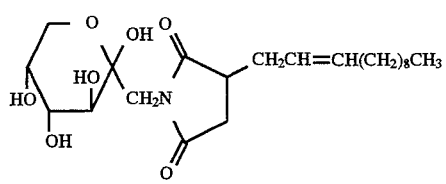

wherein based on formula (I) above:

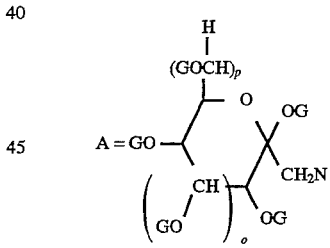

G=hydrogen (H);
R$_9$=C$_9$H$_{19}$;
W=CH$_2$;
Z=CH=CH;
c=1;
e=0;
o=0;
and p=0.

Yet another specific example of a cyclic monosaccharide alkenyl glycasuccinimide compound of the invention is dodecenyl 6-imino-6-deoxy α,β-D-methylglucopyranoside succinate having the formula:

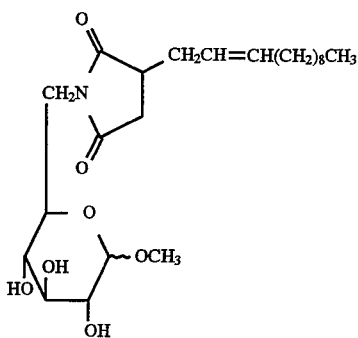

wherein based on formula (I) above:

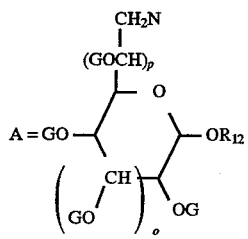

G=hydrogen (H);
$R_9=C_9H_{19}$;
$R_{12}=CH_3$;
$W=CH_2$;
$Z=CH=CH$;
c=1;
e=0;
o=1;
and p=1.

A specific example of a disaccharide alkyl glycasuccinimide compound of the invention is tetradecyl D-maltosuccinimide having the formula:

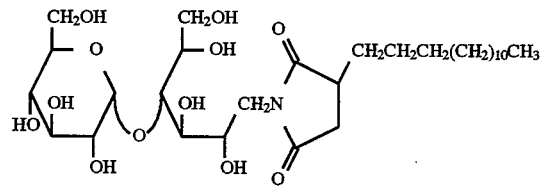

wherein based on formula (I) above:

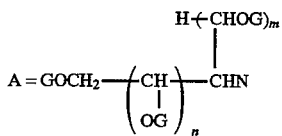

G=hydrogen (H) or glucose;
$R_9=C_{11}H_{23}$;
$W=CH_2$;
$Z=CH_2CH_2$;
c=1;
e=0;
m=0;
and n=4.

A specific example of a disaccharide alkenyl glycasuccinimide compound of the invention is dodecenyl D-lactosuccinimide having the formula:

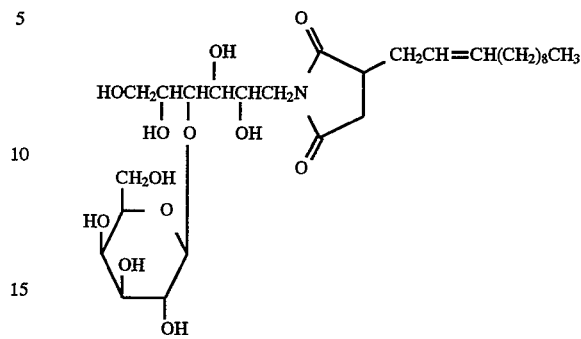

wherein based on formula (I) above:

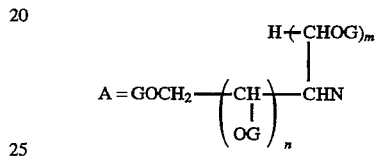

G=hydrogen (H) or galactose;
$R_9=C_9H_{19}$;
$W=CH_2$;
$Z=CH=CH$;
c=1;
e=0;
m=0;
and n=4.

Other examples of compounds of the invention are set forth below:
 alkyl and alkenyl D-erythrosuccinimide
 alkyl and alkenyl D-threosuccinimide
 alkyl and alkenyl D-ribosuccinimide
 alkyl and alkenyl D-arabinosuccinimide
 alkyl and alkenyl D-xylosuccinimide
 alkyl and alkenyl D-lyxosuccinimide
 alkyl and alkenyl D-allosuccinimide
 alkyl and alkenyl D-altrosuccinimide
 alkyl and alkenyl D-idosuccinimide
 alkyl and alkenyl D-talosuccinimide
 alkyl and alkenyl D-glucosuccinimide
 alkyl and alkenyl L-glucosuccinimide
 alkyl and alkenyl D-galactosuccinimide
 alkyl and alkenyl L-galactosuccinimide
 alkyl and alkenyl D-mannosuccinimide
 alkyl and alkenyl D-gulosuccinimide
 alkyl and alkenyl D-fructosuccinimide
 alkyl and alkenyl L-fructosuccinimide
 alkyl and alkenyl D-sorbosuccinimide
 alkyl and alkenyl L-sorbosuccinimide
 alkyl and alkenyl D-isomaltosuccinimide
 alkyl and alkenyl D-isomaltsuccinimide
 alkyl and alkenyl D-isomaltulosuccinimide
 alkyl and alkenyl D-trehalulosuccinimide
 alkyl and alkenyl D-ribulosuccinimide alkyl and alkenyl D-xylulosuccinimide
alkyl and alkenyl D-3-ketosucrosuccinimide
alkyl and alkenyl D-leucrosuccinimide
alkyl and alkenyl D-lactulosuccinimide
alkyl and alkenyl D-psicosuccinimide
alkyl and alkenyl D-rhamnosuccinimide
alkyl and alkenyl D-maltosuccinimide
alkyl and alkenyl L-maltosuccinimide
allyl and alkenyl D-lactosuccinimide
alkyl and alkenyl L-lactosuccinimide
alkyl and alkenyl D-melibiosuccinimide
alkyl and alkenyl D-cellobiosuccinimide
alkyl and alkenyl D-cellulosuccinimide
alkyl and alkenyl D-dextrosuccinimide
alkyl and alkenyl D-glucosuccinimide monooxyethylene ether
alkyl and alkenyl D-glucosuccinimide dioxyethylene ether
alkyl and alkenyl D-glucosuccinimide trioxyethylene ether
alkyl and alkenyl D-glucosuccinimide pentaoxyethylene ether
alkyl and alkenyl D-glucosuccinimide hexaoxyethylene ether
alkyl and alkenyl D-glucosuccinimide octaoxyethylene ether
alkyl and alkenyl D-glucosuccinimide nonaoxyethylene ether
alkyl and alkenyl D-glucosuccinimide decaoxyethylene ether
alkyl and alkenyl D-glucosuccinimide tetraoxypropylene ether
alkyloxy(monooxyethylene) D-glucosuccinimide
alkyloxy(dioxyethylene) D-glucosuccinimide
alkyloxy(trioxyethylene) D-glucosuccinimide
alkyloxy(pentaoxyethylene) D-glucosuccinimide
alkyloxy(heptaoxyethylene) D-glucosuccinimide
alkyloxy(decaoxyethylene) D-glucosuccinimide
alkyloxy(pentaoxypropylene) D-glucosuccinimide
alkyloxyethylamino D-glucosuccinimide
alkyloxyethylamido D-glucosuccinimide Wherein the alkyl or alkenyl group contains from about 1 to about 31 carbon atoms; preferably from about 2 to about 25 carbon atoms, even more preferably from about 3 to about 23 carbon atoms.

The G group can be hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof. Examples of M include, but are not limited to hydrogen, sodium, potassium, magnesium, ammonium, monoethanolammonium, diethanolammonium, triethanolammonium and the like.

Examples of suitable saccharides that can be reduced to a glycamine include aldotrioses, aldotetroses, aldopentoses, aldohexoses, 6-deoxyaldohexoses, aldoheptoses, ketotrioses, ketopentoses, ketohexoses, ketoheptoses, ketooctoses and ketononoses. Specific example of saccharides that fall within the above classes include, but are not limited to glyceraldehyde, erythrose, threose, ribose, arabinose, xylose, lyxose, allose, altrose, glucose, mannose, gulose, idose, galactose, talose, 6-deoxyallose, 6-deoxyaltrose, 6-deoxyglucose, 6-deoxygulose, 6-deoxytalose, fucose, rahmnose, glycergalactoheptose, glycerglucoheptose, glycermannoheptose, 1,3-dihydroxy-2-propanone, erythrulose, ribulose, xylulose, psicose, fructose, sorbose, tagatose, alloheptose, altro-3-heptulose, mannoheptulose, sedoheptulose, taloheptulose, glycerogalactooctulose, glycermannooctulose, erythrogalactononulose, erythroglucononulose, sucrose, lactose, maltose, isomaltose, isomalt, isomaltulose (palatinose), α,α-trehalose, cellobiose, gentiobiose, laminarabiose, xylobiose, inulobiose, mannobiose, chondrosine, 3-ketosucrose, leucrose, lactulose, melibiose, turnanose, trehalose, raffinose, planteose, melezitose, gentianose, maltotriose, cellotriose, panose, starchyose, verbascose, cyclohexaamylose, maltoheptanose, cellodextrin, amylose, amylodextrin, dextran, high dextrose corn syrup, high fructose corn syrup, high maltose corn syrup, xylans, mannans, starch, hemicellulose and cellulose. The saccharide may be acyclic or cyclic (including furanose, pyranose, septanose rings or mixtures thereoff), have the D or L configuration and contain a α or β glycoside group or mixtures thereof at the anomeric position.

If the $R_9$ group is an aliphatic radical (saturated or unsaturated hydrocarbon), suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, hexenyl, heptenyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the $R_{10}$ group is an aliphatic radical, suitable examples include methyl, ethyl, propyl, butyl, pentyl, hexyl, heptyl, octyl, propenyl, butenyl, pentenyl, hexenyl, heptenyl, octenyl, hydroxymethyl, hydroxyethyl, hydroxypropyl, hydroxybutyl, hydroxypentyl and hydroxyhexyl.

If the $R_{11}$ or $R_{12}$ group is an aliphatic radical, suitable examples include methyl, ethyl, propyl, butyl, pentyl, propenyl, butenyl, pentenyl, hydroxymethyl, hydroxyethyl, hydroxypropyl, hydroxybutyl and hydroxypentyl.

If the $R_9$ or $R_{10}$ is interrupted by an aromatic group, the aromatic radical may be for example, benzyl or aniline. Cycloaliphatic radicals are exemplified, but not limited to cyclopentyl and cyclohexyl. Suitable mixed aromatic aliphatic radicals are exemplified by benzylpropyl, phenylethyl, phenoxyethyl and vinylbenzyl.

When an amino group is present in the alkyl chain (wherein W=$NR_{10}$ and $R_{10}$ is hydrogen), it may be converted to the corresponding salt by reaction with, for example, an organic or inorganic acid such as hydrochloric acid, sulfuric acid, phosphoric acid, boric acid, oxalic acid, malonic acid, glutaric acid, adipic acid, sebacic acid, tricarballylic acid, 1,2,3,4-butanetetracarboxylic acid, iraconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and the like or by reaction with, for example, an alkylating or quaternizing agent such as chloromethane, dimethyl sulfate, diethyl sulfate, benzyl chloride and the like to form a salt or quaternary ammonium compound.

The alkyl- and alkenyl D-glycasuccinimide compounds of the present invention can also be ethoxylated, propoxylated or butoxylated with ethylene oxide, propylene oxide, butylene oxide or mixtures thereof to give a series of novel polyoxyalkylene sugar based nonionic surfactants.

The alkyl- and alkenyl D-glycasuccinimide compounds of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The alkyl- and alkenyl D-glycasuccinimide compounds of the present invention can also be phosphorylated with phophorus oxychloride, phosphorous pentoxide, polyphosphoric acid, phosphoric acid, phosphorus trichloride and the like as well as mixtures thereof, to give a series of novel phosphated sugar based esters (mono-, di-, and triesters as well as mixtures thereoff as anionic suffactants.

In the second embodiment of the invention, a new and improved process for the manufacture of alkyl- and alkenyl glycasuccinimide surfactants is described.

It has been found, in accordance with the present invention, that novel alkyl- and alkenyl glycasuccinimide surfactants may be readily prepared by reacting glycamines (sugar-$NH_2$) with alkyl- or alkenyl succinic anhydrides in the presence of a base catalyst at elevated temperatures (A). The invention can be more readily understood when reference is made to the general equation (A):

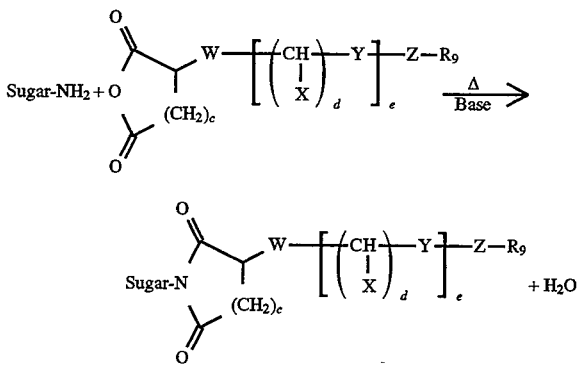

The method is especially suitable for the manufacture of alkyl- and alkenyl glycasuccinimide compounds wherein W is preferably $CH_2$ or an oxygen atom (O); X is preferably hydrogen (H), or an alkyl group having about 1 to about 3 carbon atoms; Y is preferably a $NR_{10}$, $+N(R_{10})_2$, oxygen (O) group or mixtures thereof; Z is preferably a CH=CH or $CH_2CH_2$ group; $R_9$ is preferably a straight chain saturated hydrocarbon which may be unsubstituted or substituted with an aromatic, cycloaliphatic or mixed aromatic radical comprising from about 2 to about 25 carbon atoms, $R_{10}$ is preferably hydrogen (H), a hydroxyalkyl group having about 1 to about 4 carbon atoms, a straight or branched chain, saturated or unsaturated hydrocarbon radical having about 1 to about 5 carbon atoms; c is preferably 1–3; d is preferably 1–4; and e is preferably 0–25.

Examples of preferred glycamines (1-amino-1-deoxyalditols, 2-amino-2-deoxyketitols etc.) most suitable for this method include those of the formula:

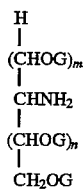

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10. Illustrative of this class include, but are not limited to glyceramine, erythramine, threamine, ribamine, arabinamine, xylamine, lyxamine, aliamine, altramine, glucamine (1-amino-1-deoxyglucitol), mannamine, gulamine, idamine, galactamine, talamine, glucoheptamine (1-amino-1-deoxyglucoheptitol), 1-amino-1-deoxyglyceroglucoheptitol, 1-amino-1-deoxyglycergalactoheptitol, 1-amino-1-deoxyglyceromannoheptitol, 1,3-dihydroxy-2-propylamine, erythrulamine (threulamine or glycerotetrulamine), ribulamine (erythropentulamine), xylulamine (threopentulamine), psicamine, fructamine (levulamine or 2-amino-2-deoxyfructitol), sorbamine (2-amino-2-deoxysorbitol), tagatamine, 2-amino-2-deoxyallohepulitol, 3-amino-3-deoxyaltro-3-heptulitol, 2-amino-2-deoxymannoheptulitol, 2-amino-2-deoxysedoheptulitol, 2-amino -2-deoxytaloheptulitol, 2-amino-2-deoxyglycerogalactooctulitol, 2-amino-2-deoxyglyceromannooctulitol, 2-amino-2-deoxyerythrogalactononulitol, 2-amino-2-deoxyerythroglucononulitol, lactamine [galactopyranosyl-α-(1-4)-1-amino-1-deoxyglucitol], maltamine [glucopyranosyl-α-(1-4)-1-amino-1-deoxyglucitol], isomaltamine-A [glucopyranosyl-α-(1-6)-1-amino-1-deoxyglucitol], isomaltamine-B [glucopyranosyl-α-(1-6)-2-amino-2-deoxyfructitol], isomaltulamine [palatinamine or glucopyranosyl-α-(1-6)-2-amino-2-deoxyfructitol], cellobiamine [glucopyranosyl-[β-(1-4)-1-amino-1-deoxyglucitol], leucramine [glucopyranosyl-α-(1–5)-2-amino-2-deoxyfructitol], gentiobiamine [glucopyranosyl-[β-(1-6)-1-amino-1-deoxyglucitol], laminarbiamine [glucopyranosyl-β-(1-3)-1-amino-1-deoxyglucitol], xylobiamine [xylopyranosyl-β-(1-4)-1-amino-1-deoxyxylitol], inulobiamine [fructopyranosyl-β-(2-1)-2-amino-2-deoxyfructitol], mannobiamine [mannopyranosyl-β-(1-4)-1-amino-1-deoxymannitol], 3-ketopalatinamine [3-ketoglucopyranosyl-α-(1-6)-2-amino-2-deoxyfructitol], arabinofuranosyl-β-(1-3)-1-amino-1-deoxyarabinitol, galactopyranosyl-α-(1-3)-1-amino-1-deoxygalactitol, maltotriamine [glucopyranosyl-α-(1-4)-glucopyranosyl-α-(1-4) -1-amino-1-deoxyglucitol], cellotriamine [glucopyranosyl-β-(1-4)-glucopyranosyl-β-(1-4)-1-amino-1-deoxyglucitol], panosamine [glucopyranosyl-α-(1-6)-glucopyranosyl-α-(1-4)-1-amino-1-deoxyglucitol], maltoheptamine [glucopyranosyl-α-(1-4)-{glucopyranosyl-α-(1-4)}$_5$-1-amino-1-deoxyglucitol], starchamine, dextramine, cellulamine, 2-amino-2-deoxyglucitol (2-amino-2-deoxysorbitol), 3-amino-3-deoxyglucitol, 4-amino-4-deoxyglucitol, 6-amino-6-deoxyglucitol, 3-amino-3-deoxyribitol, 2-amino-2-deoxygalactitol, 2-amino-2-deoxymannitol, 2-amino-2-deoxyallitol, 5-amino-5-deoxyaltritol and 6-amino-6-deoxyerythrogalactooctitol.

Examples of other glycamines (1-amino-1,6-dideoxyalditols) suitable for this method include those of the formula:

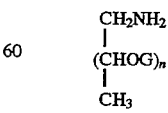

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about n is from about 1 to about 6, m is from about 0 to about 8 and the sum of n and m are from about 0 to about 10. Illustrative of this class include, but are not limited to 1-amino-1,6-dideoxyallitol, 1-amino-1,6-dideoxyaltritol, 1-amino-1,6-dideoxyglucitol, 1-amino-1,6-dideoxygulitol, 1-amino-1,6-di-deoxytalitol, 1-amino-1,6-dideoxyfucitol and 1-amino-1,6-dideoxyrhamnitol.

Still other examples of glycamines (1-amino-1-deoxyketoses) suitable for this method include those of the formula:

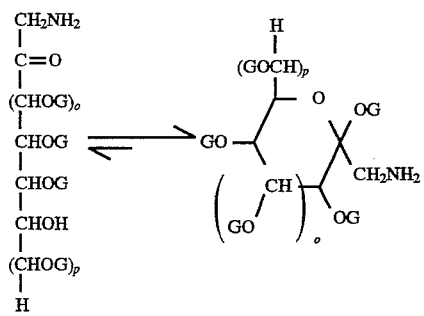

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4. These glycamines are described as Amadori rearrangement products and methods for preparing such are disclosed in Methods in Carbohydr. Chem. 2, 99, (1963) to Hodge and Fisher which is incorporated herein by reference. Illustrative of this class include, but are not limited to 1-amino-1-deoxyribulose, 1-amino-1-deoxyxylulose, 1-amino-1-deoxypsicose, 1-amino-1-deoxyfructose [1-amino-1-deoxylevulose), 1-amino-1-deoxyfructose hydrochloride, 1-amino-1-deoxyfructose acetate salt, 1-amino-1-deoxyfructose oxalate salt, 1-amino-1-deoxysorbose, 1-amino-1-deoxytagatose, 1-amino-1-deoxyalloheptulose, 1-amino-1-deoxymannoheptulose, 1-amino-1-deoxysedoheptulose, 1-amino-1-deoxytaloheptulose, 1-amino-1-deoxyglycerogalactooctulose, 1-amino-1-deoxyglyceromannooctulose, 1-amino-1-deoxyerythrogalactononulose, galactopyranosyl-β-(1-4)-1-amino-1-deoxyfructose, glucopyranosyl-α-(1-4)-1-amino-1-deoxyfructose, glucopyranosyl-β-(1-4)-glucopyranosyl-β-(1-4)-1-amino-1-deoxyfructose and glucopyranosyl-α-(1-4)-{glucopyranosyl-α-(1-4)}$_4$-1-amino-1-deoxyfructose.

Still other examples of glycamines (Z-amino-Z-deoxyaldoses) suitable for this method include those of the formula:

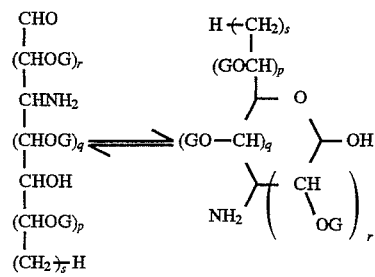

wherein G is hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof; M is hydrogen (H), an alkali metal, alkaline earth metal, ammonium, alkyl substituted ammonium or mono-, di-, trialkanolammonium group with about 1 to about 5 carbon atoms; a and b are each from about 0 to about 35 and the sum of a and b are from about 0 to about 35; p and q are each from about 0 to about 3, r is from about 0 to about 4, s is from about 0 to about 1 and the sum of p, q and r are from about 0 to about 6. Illustrative of this class include, but are not limited to 3-amino-3-deoxyribose, glucosamine (chitosamine or 2-amino-2-deoxyglucose}, glucosamine hydrochloride, glucosamine acetate (2-acetamido-2-deoxyglucose), glucosamine-2-sulfate, glucosamine-3-sulfate, glucosamine-6-sulfate, glueosamine-2,3-disulfate, glucosamine-2,6-disulfate, glucosamine-1-phosphate, glucosamine-6-phosphate, kanosamine {3-amino-3-deoxyglucose), 4-amino-4-deoxyglucose, 2-amino-2,6-dideoxyglucose, 3-amino-3,6-dideoxyglucose, mannosamine (2-amino-2-deoxymannose), mycosamine (2-amino-2,6-dideoxymannose), 3-amino-3,6-dideoxymannose, gulosamine (2-amino-2-deoxygulose), galactosamine (chondrosamine or 2-amino-2-deoxygalaetose), fucosamine (2-amino-2,6-dideoxygalactose), 3-amino-3,6-dideoxygalactose, talosamine (2-amino-2-deoxytalose), pneumosamine (2-amino-2,6-dideoxytalose), daunosamine (3-amino-2,3,6-trideoxylyxohexose), chitobiose [2-amino-2-deoxy-4-O-(2-amino-2-deoxy-β-glucopyranosyl)glucopyranose], 2-amino-2-deoxy-4-O-(α-glucopyranosyl)glucopyranose, 2-amino-2-deoxy-4-O-(2-amino-2-deoxy-β-glucopyranosyl)$_4$glucopyranose, chitin and chitosan.

Still other examples of glycamines (1-amino-1-deoxyaldoses and 2-amino-2-deoxyketoses) suitable for this method include those of the formula:

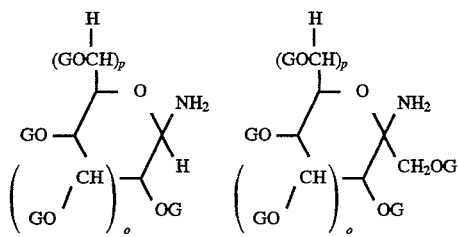

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4. Illustrative of this class include, but are not limited to 1-amino-1-deoxyribose, 1-amino-1-deoxyxylose, 1-amino-1-deoxyglucose, 1-amino-1-deoxymannose, 1-amino-1-deoxygulose, 1-amino-1-deoxyidose, 1-amino-1-deoxygalactose, 1-amino-1-deoxyglucoheptose, 1-amino-1-deoxyglyceroglucoheptose, 2-amino-2-deoxyfrucose, 2-amino-2-deoxysorbose, 1-amino-1-deoxylactose [galactopyranosyl-β-(1-4)-1-amino-1-deoxyglucose], 1-amino-1-deoxymaltose [glucopyranosyl-α-(1-4)-1-amino-1-deoxyglucose], 1-amino-1-deoxymaltotriose [glucopyranosyl-α-(1-4)-glucopyranosyl-α-(1-4)-1-amino-1-deoxyglucose]and 1-amino-1-deoxymaltoheptose [glucopyranosyl-α-(1-4)-{glucopyranosyl-α-(1-4)}$_5$-1-amino-1-deoxyglucose].

Still other examples of glycamines (Z-amino-Z-deoxyglycosides) suitable for this method include those of the formula:

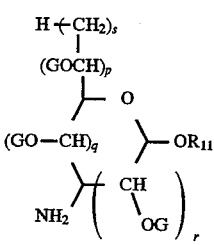

wherein G is hydrogen (H), a $SO_3M$, $PO_3M_2$, $(CH_2CH_2)_aH$ or $(CH_2CHCH_3O)_bH$ group, a mono-, di-, oligo- or polysaccharide or mixtures thereof; M is hydrogen (H), an alkali metal, alkaline earth metal, ammonium, alkyl substituted ammonium or mono-, di-, trialkanolammonium group with about 1 to about 5 carbon atoms; $R_{11}$ is hydrogen (H), or an alkyl, alkenyl or hydroxyalkyl group having about 1 to about 5 carbon atoms; a and b are each from about 0 to about 35 and the sum of a and b are from about 0 to about 35; p and q are each from about 0 to about 3, r is from about 0 to about 4, s is from about 0 to about 1 and the sum of p, q and r are from about 0 to about 6. Illustrative of this class include, but are not limited to 3-amino-3-deoxymethylriboside, methylglucosidoamine (2-amino-2-deoxymethylglucoside), 2-amino-2-deoxymethylglucoside hydrochloride, 2-amino-2-deoxyethylglucoside, 2-amino-2-deoxypropylglucoside, 2-amino-2-deoxyhydroxyethylglucoside, 2-acetamido-2-deoxymethylglucoside, methylglucosidoamine-6-disulfate, methylglucosidoamine-6-phosphate, 3-amino-3-deoxyethylglucoside, 4-amino-4-deoxybutylglucoside, 2-amino-2-deoxymethylmannoside, 2-amino-2-deoxyhydroxyethylguloside, 2-amino-2,6-dideoxyethylgalactoside, 2-amino-2-deoxy-4-(2-amino-2-deoxy-β-glucopyranosyl)methylglucoside and 2-amino-2-deoxy-4-O-(2-amino-2-deoxy-β-glucopyranosyl)₄methylglucoside.

Still other examples of glycamines (6-amino-6-deoxyaldoses, 6-amino-6-deoxyketoses, 6-amino-6-deoxyglycosides etc.) suitable for this method include those of the formula:

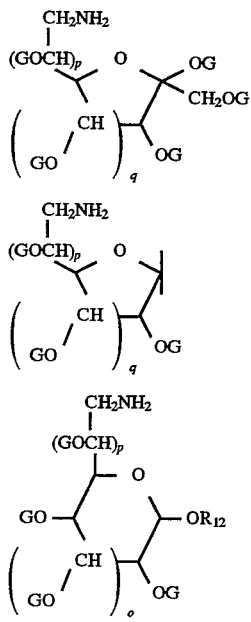

wherein G is hydrogen (H), a $(CH_2CH_2O)_aH$ or $(CH_2CHCH_3O)_bH$ group, a mono-, di-, oligo- or polysaccharide or mixtures thereof; $R_{12}$ is hydrogen (H), or an alkyl, alkenyl or hydroxyalkyl group having about 1 to about 5 carbon atoms; a and b are each from about 0 to about 35 and the sum of a and b are from about 0 to about 35; o is from about 0 to about 2, p is from about 0 to about 4 and q is from about 0 to about 3. Illustrative of this class include, but are not limited to 5-amino-5-deoxyribose, 5-amino-5-deoxyxylose, 6-amino-6-deoxyallose, 6-amino-6-deoxyaltrose, 6-amino-6-deoxyglucose, 6-amino-6-deoxyglucose hydrochloride, 6-amino-6-deoxymethylglucoside, 6-amino-6-deoxyethylglucoside, 6-amino-6-deoxymannose, 6-amino-6-deoxygulose, 6-amino-6-deoxyldose, 6-amino-6-deoxygalactose, 6-amino-6-deoxytalose, 7-amino-7-deoxyglucoheptose, 7-amino-7-deoxy-glyceroglucoheptose, 7-amino-7-deoxyglycergalactoheptose, 7-amino-7-deoxyglyceromannoheptose, 6-amino-6-deoxyfructose, 7-amino-7-deoxyalloheptulose, 7-amino-7-deoxymannoheptulose, 7-amino-7-deoxysedo-heptulose, 7-amino-7-deoxytaloheptulose, 8-amino-8-deoxyglycerogalactooctulose, 8-amino-8-deoxyglyceromannooctulose, 9-amino-9-deoxyerythrogalactononulose, 9-amino-9-deoxyerythroglucononulose, galactopyranosyl-β-(1-4)-6-amino-6-deoxyglucose, 6-amino-6-deoxygalactose-β-(1-4)-glucopyranose, 6-amino-6-deoxygalactose-β-(1-4)-6-amino-6-deoxyglucose, glucopyranosyl-β-(1-4)-6-amino-6-deoxyglucose, 6-amino-6-deoxyglucose-α-(1-4)-glucopyranose, 1-amino-1-deoxy-β-fructofuranosyl-α-glucopyranoside, 6-amino-6-deoxy-α-fructofuranosyl-β-glucopyranoside, β-fructofuranosyl-α-6-amino-6-deoxyglucopyranoside and glucopyranosyl-α-(1-4)-{glucopyranosyl-α-(1-4)}₅-6-amino-6-deoxyglucose.

Yet other examples of glycamines suitable for this method include the Z-amino-Z-deoxyketoses wherein Z is from about 2 to about 8. Illustrative of this class include, but are not limited 5-amino-5-deoxyxylohexulose and 6-amino-6-deoxyxylohexulose.

Many additional examples of glycamines that are useful in the present invention are described in "Carbohydrates" edited by Collins, published by Chapman and Hall Ltd., (1987) and "The Carbohydrates, Chemistry and Biochemistry" edited by Pigman and Horton, 2nd Edition, Volumes IA, IIA, IB and IIB, published by Academic Press Inc., (1972); all of which are incorporated herein by reference.

Of the above described glycamines, those of the following formulas are most highly preferred:

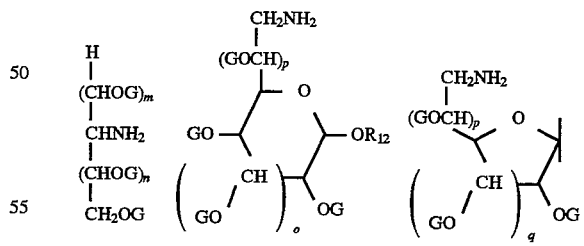

wherein G is hydrogen (H) or a monosaccharide; $R_{12}$ is hydrogen (H) or an alkyl, alkenyl or hydroxyalkyl group having from about 1 to about 4 carbon atoms: m=0; n=1–4; o=0–1; p=0–1 and q=1.

Examples of suitable alkenyl succinic anhydrides, which are prepared by the condensation of maleic anhydride with an alkene (olefin), that are useful in the present method include, but are not limited to octenylsuccinic anhydride, diisobutylenesuccinic anhydride, nonenylsuccinic anhydride, decenylsuccinic anhydride, undecenylsuccinic anhydride, dodecenylsuccinic arthydride, trIisobutylenesuccinic anhydride, tridecenylsuccInic anhydride, tetradecenylsuccinic anhydride, pentadecenylsuccinic anhydride, hexadecenylsuccinic anhydride, tetraisobutylenesuccinic anhydride, heptadecenylsuccinic anhydride, octadecenylsuccinic anhydride and mixtures thereof.

Examples of suitable alkyl succinic anhydrides, which are prepared by hydrogenating alkenyl succinic anhydrides, that are useful in the present method include, but are not limited to octylsuccinic anhydride, nonyl- succinic anhydride, decylsuccinic anhydride, undecylsuccinic anhydride, dodecylsuccinic anhydride, tridecylsuccinic arthydride, tetradecylsuccinic anhydride, pentadecylsuccinic anhydride, hexadecylsuccinic anhydride, hexadecylsuccinic anhydride, octadecylsuccinic anhydride, isodecylsuccinic anhydride, isododecylsuccinic anhydride, isotridecylsuccinic anhydride, isotetradecylsuccinic anhydride, octyloxysuccinic anhydride, nonyloxysuccinic anhydride, decyloxysuccinic anhydride, undecyloxysuccinic anhydride, dodecyloxysuccinic anhydride, dodecyloxy(dioxyethylene)succinic anhydride, dodecyloxy(trioxyethylene)succinic anhydride, tetradecyloxy(tetraoxyethylene)succinic anhydride, tetradecyloxy(hexaoxyethylene)succinic anhydride, tetradecyloxy(pentaoxypropylene)succinic anhydride, dodecyloxy(dioxyethylenetrioxypropylene)succinic anhydride as well as $C_8$–$C_{18}$ alkyl hydroxysuccinic anhydride, $C_8$–$C_{18}$ alkyl hydroxy sulfonatesuccinic anhydride, $C_8$–$C_{18}$ alkyl epoxysuccinic anhydride, $C_8$–$C_{18}$ alkyl dichlorosuccinic arthydride, $C_8$–$C_{18}$ alkyl sulfonatesuccinic anhydride, adipic arthydride and mixtures thereof.

The alkyl- and alkenyl succinic acids (dicarboxylic acids), which are prepared by the condensation of maleic acid or fumaric acid with an alkene or by hydrolysis of an alkyl- or alkenyl succinic anhydride, are useful as well however, the methyl, ethyl, propyl, isopropanol, butyl, hexyl esters and the like of alkyl- and alkenyl succinic acids are preferred, since products obtained from these materials are isolated on good yield and color.

Other examples of alkyl- and alkenyl dicarboxylic acids useful in the present method include those obtained by the condensation of iraconic acid, citraconic acid, mesaconic acid, trans-glutaconic acid, trans-β-hydromuconic acid, aconitic acid and the like with an alkene. Specific examples include, but are not limited to 2-octenyl-2-methylsuccinic acid, 2-decenyl-2-methylsuccinic acid, 2-decyl-2-methylsuccinic acid, 2-dodecenyl-2-methylsuccinic acid, 2-tetradecenyl-2-methylsuccinic acid, 2-octenyl-3-methylsuccinic acid, 2-decenyl-3-methylsuccinic acid, 2-dodecenyl-3-methylsuccinic acid, 2-tetradecenyl-3-methylsuccinic acid, 2-octenylglutaric acid, 2-decenylglutaric acid, 2-decylglutaric acid, 2-dodecenylglutaric acid, 2-tetradecenylglutaric acid, 3ooctenylglutaric acid, 3-decenylglutaric acid, 3-decylglutaric acid (3-decylpentan-1,5-dioic acid), 3-dodecenylglutaric acid, 3-tetradecenylglutaric acid, 3-octenyladipic acid, 3-decenyladipic acid, 3-decyladipic acid, 3-dodecenyladipic acid, 3-tetradecenyladipic acid, octylmalonic acid, decylmalonic acid, dodecylmalonic acid, tetradecylmalonic acid, dodecenylmalonic acid, 2-octylsuberic acid, 4-butyldecan-1,10-dioic acid, and the like. Again, the methyl, ethyl, propyl, isopropanol, butyl or hexyl esters of these alkyl- and alkenyl dicarboxylic acids are also preferred.

Methods for preparing alkyl- and alkenyl anhydrides, dicarboxylic acids and the like are disclosed in U.S. Pat. Nos. 2,283,214 and 2,380,699 to Kyrides et al. both of which are incorporated herein by reference. Of the above described hydrophobic substrates, the anhydrides are preferred for use herein.

Within the process of the invention, it is desirable to use water-free reaction components, although small amounts of water (from about 1% to about 15% by weight) can be tolerated.

Also, within the process of the invention, the glycamine can be added progressively to the arthydride, or the anhydride can be added progressively to the glycamine, preferably however, both reagents are added in full amount at the beginning of the reaction. The glycamine can be used in molar excess relative to the anhydride, or the arthydride can be used in molar excess relative to the glycamine, preferably however, as seen in Examples 2 through 14, the reagents are used in stoichiometric molar amounts.

The glycamine or the arthydride is preferably in crystalline to granular form, however solid, flake, paste, gel or liquid form can be used as well.

The reaction may be performed at or below room temperature, however shorter reaction times can be achieved at elevated temperature and is usually preferred. Favorable reaction temperatures are from about 30° C. to about 300° C., preferably from about 40° C. to about 250° C., most preferably from about 60° C. to about 200° C.

The reaction can be carried out under reduced pressure to assist in the removal of water, however, it is preferably carried out at atmospheric pressure and under an inert gas blanket such as nitrogen, argon or helium, most preferably it is carried out at atmospheric pressure.

Optionally a catalyst used to accelerate the rate of the reaction is generally classified as an organic or inorganic base. Examples of suitable base catalysts useful in the present method include, but are not limited to sodium hydroxide, potassium hydroxide, ammonium hydroxide, calcium hydroxide, magnesium hydroxide, sodium metal, potassium metal, sodium methoxide, potassium methoxide, sodium ethoxide, potassium ethoxide, sodium carbonate, potassium carbonate, ammonium carbonate, magnesium carbonate, calcium carbonate, lithium carbonate, sodium bicarbonate, potassium bicarbonate, ammonium bicarbonate, magnesium bicarbonate, calcium bicarbonate, trisodium phosphate, tripotassium phosphate, tetrasodium pyrophosphate, tetrapotassium pyrophosphate, pentasodium tripolyphosphate, pentapotassium tripolyphosphate, disodium tartrate, dipotassium tartrate, sodium potassium tartrate, trisodium citrate, tripotassium citrate, sodium acetate, potassium acetate, sodium valerate, sodium laurate, potassium laurate, sodium myristate, potassium myristate, sodium stearate, sodium oleate, sodium 12-hydroxydodeconate, sodium 2,2-dimethylbutyrate, disodium oxalate, dipotassium oxalate, disodium malonate, dipotassium malonate, disodium succinate, dipotassium succinate, disodium dodecyl succinate, disodium glutarate, dipotassium glutarate, disodium 1,12-dodecanedicarboxylate, trisodium tricarballylate, tripotassium tricarballylate, tetrasodium 1,2,3,4-butanetetracarboxylate, tetrapotassium 1,2,3,4-butanetetracarboxylate, disodium itaconate, dipotassium itaconate, disodium maleate, dipotassium maleate, disodium fumarate, dipotassium fumarate, disodium malate, disodium agaricate, dipotassium agaricate, sodium ethoxyacetate, sodium glyoxylate, sodium 4-acetylbutyrate, sodium cyclohexylacetate, trisodium 1,3,5-cyclohexanetricarboxylate, sodium basic silicates, potassium basic silicates, sodium basic aluminosilicates, potassium basic aluminosilicates, sodium lactate, potassium lactate, ammonium lactate, sodium glycinate, sodium dimethylglycinate, pentasodium diethylenetriaminepentaacetate (DTPA), tetrasodium ethylenediaminetetraacetate (EDTA), tetrapotassium ethylenediaminetetraacetate, calcium disodium ethylenediaminetetraacelate, triethylamine, tilpropylamine, tributylamine, trioctylamine, N,N-dimethyldodecylamine, N,N'-diethylethylenediamine, N,N-diethyl-N'-methylethylenediamine, N,N,N',N'-tetramethylethylenediamine, N,N,N',N'-tetraethylethylenediamine, N,N,N',N'-tetramethylethylenediamine, N,N,N',N'-tetraethyl-1,3-propanediamine, monoethanolamine, diethanolamine, triethanolamine, pyridine, morpholine, picoline, collidine, ethylpiperidine diethylcyclohexylamine and the like. Mixtures of base catalysts can be also used as well and may be preferred in certain cases. Preferred base catalysts include sodium hydroxide, sodium methoxide, sodium carbonate, potassium carbonate, sodium bicarbonate, trisodium titrate, sodium laurate, disodium oxalate, triethylamin, tripropylamine, monoethanolamine, diethanolamine, tilethanolamine and mixtures thereof.

The base catalyst can be added at any time during the reaction, however, It is preferably added at the beginning of the reaction and in full amount. The molar ratio of glycamine to base catalyst is from about 500:1 to about 1:1, preferably from about 250:1 to about 5:1, most preferably from about 150:1 to about 10:1.

The substrates are reacted with intensive stirring for several hours, preferably from about 0.5 hour to about 20 hours, more preferably from about 1 hour to about 15 hours, most preferably when the water of reaction is completely removed and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), fast atom bombardment mass spectrometry (FAB MS), or high pressure liquid chromatography (HPLC).

In general, water or an organic solvent can be used to perform the reaction of the present invention, however, these materials are not necessary and are therefore not preferred. However, when an organic solvent is used, the quantity of solvent should be sufficient to dissolve the carbohydrate and anhydride, but otherwise this is not an essential condition. An organic solvent may become necessary when heat sensitive carbohydrates are used (e.g., certain Z-deoxy-Z-aminoaldoses or ketoses). Typical levels of solvent used are from about 5% to about 95%, preferably from about 15% to about 75%, most preferably from about 30% to about 50% by weight of the total reaction mixture. Preferably the solvent is removed (after the reaction is complete) by known procedures such as simple distillation, vacuum distillation or rotaevaporation. When water is used, it may be removed by freeze drying, spray drying, or vacuum distillation, however, it may be more economical to leave the water in and use it as a diluent making the product a pureable liquid. Typical levels of water used as a reaction solvent or diluent are from about 5% to about 95%, preferably from about 15% to about 65%, most preferably from about 25% to about 50% by weight of the total reaction mixture.

In general, the nonionic alkyl- and alkenyl glycasuccinimide surfactants of the present invention are usually isolated as solids, however, when syrups are obtained, crystallization may be enhanced by the addition of an organic solvent. The resulting product is subsequently filtered, washed with an organic solvent and air or vacuum dried.

Optionally, further purification of (solid) alkyl- and alkenyl glycasuccinimide surfactants can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Typical reaction solvents, crystallization solvents and recrystallization solvents that may be used include, but are not limited to acetic acid, acetone, acetonitrile, butanol, sec-butanol, tert-butanol, burylacerate, butyl chloride, chloroform, cyclohexane, cyclopentane, dimethylformaide (DMF), dimethylacetamide, dimethylsulfoxide (DMSO), 2-ethoxyethanol, ethylacetate, ethyl ether, ethylene glycol dimethyl ether (glyme), pentane, hexane, heptane, hexadecane, methanol, 2-methoxyethanol, 2-methoxyethyl acetate, methylethylketone (MEK), methylisoamylketone, methylisobutylketone, butylmethylketone, diisobutylketone, N-methyl-2-pyrrolidine, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentylacetate, carbon disulfide, 1-chlorobutane, 1,2-dichloroethane, 1,2-dimethoxyethane, glycerol, methylcyclohexane, ethylene glycol, furan, 1,2-dimethoxyethane, propylene glycol, 1-chloro-1,1-difluoroethane, isopropylbenzene (cumene), cyclohexanol, cyclohexanone, 4-hydroxy-4-methyl-2-pentanone (diacetone alcohol), diethylene glycol, diisopropyl ether, ethylene glycol monobutyl ether (2-butoxyethanol), ethylene glycol monomethyl ether (2-methoxyethanol), hexylene glycol, isopentylacetate, isobutylacetate, isopropylacetate, methylacetate, methylpentylketone, and the like, however, alcohols are the preferred reaction solvents and acetates or alcohols are the preferred recrystallization solvents. Mixtures of solvents can be used as well and may be preferred in certain cases.

When the reaction is complete, the catalyst may be optionally neutralized with an organic or inorganic acid. Examples of suitable neutralizing acids include, but are not limited to hydrochloric acid, sulfuric acid, phosphoric acid, boric acid, nitric acid, oxalic acid, malonic acid, glutaric acid, adipic acid, sebacic acid, tricarballylic acid, 1,2,3,4-butanetetracarboxylic acid, iraconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, gluconic acid, glucoheptonic acid, lactobionic acid, maltobionic acid, coconut fatty acid, lauric acid, myristic acid, palmitic acid, valeric acid, 2-propylpentanoic acid, succinic acid, dodecenyl succinic acid, arotonic crotonic acid, tiglic acid, glycolic acid, ketomalonic acid, methoxyacetic acid, ethoxyacetic acid, 3-methoxypropionic acid, 6-nitrocaproic acid, levulinic acid, chelidonic acid, cyclobutanecarboxylic acid, 1,1-cyclohexanediacetic acid, glycine, phenylacetic acid, 3-benzoylpropionic acid, S-benzylthioglycolic acid, phenylmalonic acid, 2-hydroxyphenylacetic acid, toluenesulfonic acid, S-sulfobenzoic acid, 5-sulfoisophthalic acid, $C_8$ to $C_{18}$ is alkylbenzenesulfonic acid, methanesulfonic acid, ethanesulfonic acid, propanesulfonic acid, $C_8$ to $C_{18}$ alkyl sulfonic acid, 3-hydroxy-1-propanesulfonic acid, isethionic acid, sulfur trioxide, artionic surfactants in the acid form, ion exchange resin and the like. Mixtures of acids can be used as well. Preferred neutralizing acids include hydrochloric acid, oxalic acid, tartaric acid, citric acid, formic acid, lactic acid, lauric acid, dodecenyl succinic acid, $C_8$ to $C_{18}$ alkylbenzenesulfonic acid and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof, at about 0° C. to about 35° C.

Bleaching is sometimes required but not always necessary, since compounds of the invention are usually of good color. Bleaching agents or peroxy compounds that may be used to further improve color are hydrogen peroxide, sodium hypochlorite, potassium hypochlorite, calcium hypochlorite, lithium hypochlorite, dibasic magenesium hypochlorite, sodium hypobromite, chlorinated trisodium phosphate, hypochlorous acid, chlorine dioxide, sodium percarbonate, potassium percarbonate, sodium perborate monohydrate, sodium perborate tetrahydrate, oxone, t-butyl hydroperoxide, benzoyl peroxide, bis(trimethylsilyl) peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxymaleic acid, peroxypropionic acid, peroxylauric acid and the like. However, hydrogen peroxide and hydrogen peroxide liberating or generating compounds are preferred. Bleaching may be optionally done in water or in an inert organic solvent before or during the reaction or after the reaction is complete, preferably however, bleaching is done after the reaction is complete at about 0° C. to about 50° C. and in water or an organic solvent. Typical levels of bleaching agent are from about 0.01% to about 10%, preferably from about 0.02% to about 7%, even more preferably from about 0.03% to about 5% by weight of the total reaction mixture.

Color improvement may also be carried out by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisulfate (pyrosulfite) and mixtures thereof. Suitable salt counter ions include alkali metal, alkaline earth metal, ammonium, alkyl- or hydroxyalkylammonium cations and mixtures thereof. Specific examples include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite and potassium metabisulfite. Sulfur dioxide, sulfurous acid and sodium sulfoxylate formaldehyde are useful as well.

The second class of reducing agents includes those compounds having hydrogen in the -1 oxidation state and show a negative oxidation potential relative to hydrogen. Illustrative of this class are sodium hydride, potassium hydride, calcium hydride, lithium hydride, magnesium hydride, sodium borohydride, sodium cyano borohydride potassium borohydride, lithium borohydride, magenesium borohydride, alkyl- and alkoxy borohydrides, aluminum hydride, sodium aluminum hydride, potassium aluminum hydride, calcium aluminium hydride, lithium aluminum hydride, alkyl- and alkoxy aluminum hydrides such as sodium dihydrobis(2-methoxyethoxy)aluminate, diboranes and mixtures thereof. Particularly preferred among the foregoing are the bisulfites and borohydrides, most especially preferred are sodium bisulfite and sodium borohydride and mixtures thereof. Reduction may be optionally done in water or in an inert organic solvent before or during the reaction or after the reaction is complete, preferably however, reduction is done without water or an organic solvent and after the reaction is complete at about 0° C. to about 200° C. Typical levels of reducing agent are from about 0.01% to about 12%, preferably from about 0.02% to about 9%, even more preferably from about 0.03% to about 7% by weight of the total reaction mixture.

In the third embodiment of the invention, a similar class of nonionic glycasuccinamide surfactant is described, specifically alkyl- and alkenyl bis(glyca)succinamides.

An alkyl- or alkenyl bis(glyca)succinamide is defined as an alkyl- or alkenyl amide of an 1-amino-1-deoxyalditol, 1-amino-1,6-dideoxyalditol or 2-amino-2-deoxyketitol, which in turn, is defined as a sugar substance in which the pseudoaldehyde or pseudoketose group, generally found at the $C_1$ or $C_2$ position of the sugar, has been reduced to an amino group through a reductive amination reaction with ammonia and hydrogen in the presence of a metal catalyst such as nickel. The reaction is typically done in water or organic solvent, but is usually done in a mixture of both. Methods of preparing such glycamines are well known in the art and are described in the J. Chem. Soc. 1682, (1922) to Ling et al.; J. Amer. Chem. Soc. 62, 3315, (1940) to Wayne et al., 72, 5416, (1950) to Holly et al., 79, 3541, (1957) to Kagan et al.; Methods in Carbohydr. Chem. 2, 79, (1963) to Long et al.; U.S. Pat. Nos. 2,016,962 to Flint et al., 2,621,175 to Holly et al.; and EP Application No. 0,536,939 to Beck all of which are incorporated herein by reference.

An alkyl- or alkenyl bis(glyca)succinamide can also be defined as an alkyl- or alkenyl amide of an 1-alkylamino-1-deoxyalditol, 1-alkylamino-1,6-dideoxyalditol or 2-alkylamino-2-deoxyketitol, which in turn, is defined as a sugar substance in which the pseudoaldehyde or pseudoketose group, generally found at the $C_1$ or $C_2$ position of the sugar, has been reduced to an alkylamino group through a reductive amination reaction with an $C_1$–$C_{28}$ alkylamine and hydrogen in the presence of a metal catalyst such as nickel. The reaction is typically done in water or organic solvent, but is preferably done in a mixture of both. Methods of preparing such glycammes are well known in the art and are described in U.S. Pat. Nos. 5,334,764 to Scheibel et al., 2,016,962 to Flint et al., J. Amer. Chem. Soc. 66, 483 (1944) and J. Dispersion Science and Technology 12 (3&4), 227, (1991) all of which are incorporated herein by reference.

An alkyl- or alkenyl bis(glyca)succinimide can be further defined as an alkyl- or alkenyl amide of a Z-amino-Z-deoxyalditol (hydrogenated aldosamine or ketosamine), wherein Z is from about 2 to about 8, which in turn, is defined as a sugar substance in which the pseudoaldehyde or pseudoketose group, generally found at the $C_1$ or $C_2$ position of the sugar, has been reduced to a hydroxyl group with hydrogen in the presence of a metal catalyst such as nickel or platinum or a metal reducing agent such as sodium borohydride. The reaction is typically done in water. Methods of preparing such glycamines are well known in the art and are described in the J. Biol. Chem. 120, 577, (1937) to Levene et al.: Helv. Chim. Acta. 20, 627, (1937) to Karrer et al.: Chem. Ber. 102, 459, (1969) to Paulsen et al.: and U.S. Pat. No. 4,307,072 to Smith all of which are incorporated herein by reference.

An alkyl- or alkenyl bis(glyca)succinamide can be even further defined as an alkyl- or alkenyl amide of a Z-amino-Z-deoxyaldose, Z-amino-Z-deoxy-ketose, Z-amino-Z-deoxyglycoside, Z-alkylamino-Z-deoxyaldose, Z-alkylamino-Z-deoxyketose, Z-alkylamino-Z-deoxyglycoside, wherein Z is from about 1 to about 8. Methods of preparing or isolating such glycamines are well known in the art and are described in Adv. Carbohydr. Chem. 7, 247, (1957) to Foster et al., 13, 189, (1958) to Jeanloz,; Methods in Carbohydr. Chem. 1,228, (1962) to Stacey et al.: Chem. Ber. 103, 1599, (1970) to Paulsen et al.; Can. J. Chem. 46, 1586, (1968) to Sowa et al.; J. Am. Chem. Soc. 81, 3716, (1959) to Wolftom et al.; Helv. Chim. Acta 4.6, 282, (1963) to Hardegger et al., 40, 342, (1957) to Druey et al.; Ann. 148, 600, (1956) to Kuhn et al,; and J. Org. Chem. 26, 603, (1961) to Zaugg all of which are incorporated herein by reference.

A bis(glyca)succinamide may be based on carbohydrates comprising one saccharide unit [e.g., bis(ribo)succinamides, bis(gluco)succinamides, bis(2-deoxy-2-aminosorbitol) succinamides, bis(glucohepto)succinamides or bis(fructo)succinamides], two saccharide units [e.g., bis(lacto)succinamides, bis(malto)succinamides or bis(cellobio)succinamides], three saccharide units [e.g., bis(maltotrio)succinamides or bis(cellotrio)succinamides] or they may be based on compounds comprising more than three saccharide units [e.g., bis(maltohepto)succinamides]. It should be noted that any carbohydrate can be used as long as the sugar has an amino group or a pseudoaldehyde or pseudoketose group available for reduction to an amino group.

In general, the nonionic alkyl- and alkenyl bis(glyca)succinamide surfactants are of the formula:

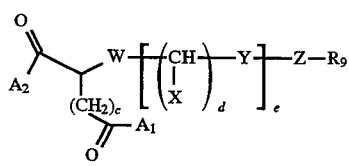

(II)

wherein:

$A_2$ represents the following structures which are attached to the succinate ring via the nitrogen (N) atom;

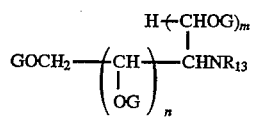

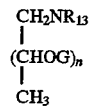

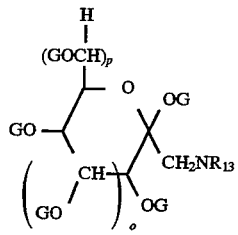

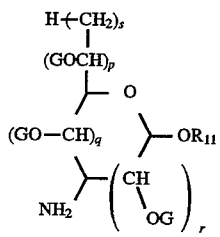

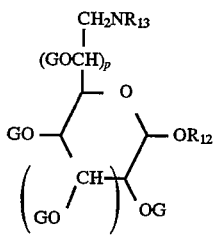

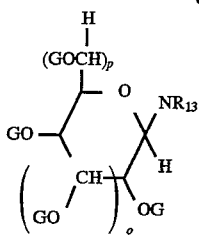

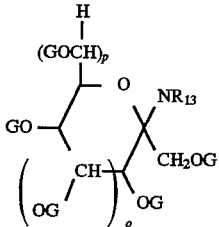

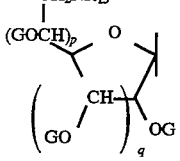

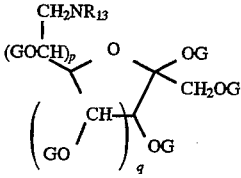

$A_1$ is $A_2$, $OR_{12}$, $O(CH_2CH_2O)_aR_9$, $O(CH_2CHCH_3O)_bR_{10}$, $N(R_{12})_2$, $NH[(CH-X)_dY]_eR_9$ group or mixtures thereof;

$R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms;

G, M, W, X, Y, Z, $R_9$, $R_{10}$, $R_{11}$, $R_{12}$, a, b, c, d, e, m, n, o, p, q, r, and s are the same as defined for formula (I) above.

More preferably:

$A_2$ represents the following structures which are attached to the succinate ring via the nitrogen (N) atom;

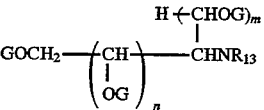

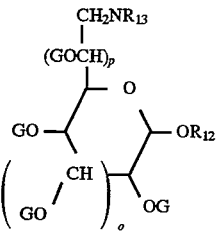

-continued

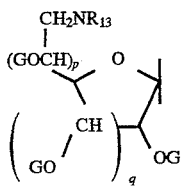

$A_1$ is $A_2$, $OR_{12}$, $N(R_{12})_2$ group or mixtures thereof;

G is hydrogen (H), a $(CH_2CH_2O)_aH$ or $(CH_2CHCH_3O)_bH$ group, a monosaccharide or mixtures thereof;

X is hydrogen (H), an alkyl group having about 1 to about 2 carbon atoms or mixtures thereof;

Y is an oxygen atom (O);

Z is a CH=CH, $CH_2CH_2$ group or mixtures thereof;

$R_9$ is a straight or branched chain saturated hydrocarbon radical having about 3 to about 23 carbon atoms;

$R_{12}$ is hydrogen (H), an alkyl, alkenyl or hydroxyalkyl group having about 1 to about 4 carbon atoms or mixtures thereof;

$R_{13}$ is hydrogen (H), a straight or branched chain saturated or unsaturated hydrocarbon which may be unsubstituted or substituted with a hydroxyl, polyhydroxyl radical having about 1 to about 6 carbon atoms;

a=0–15;
b=0–15;
c=1–2;
d=1–4;
e=0–15;
m=0–5;
n=1–5;
o=0–1;
p=0–2;
and q=0–2.

A specific example of a monosaccharide alkyl bis(glyca) succinamide compound of the invention is dodecyloxy bis (D-gluco)succinamide having the formula:

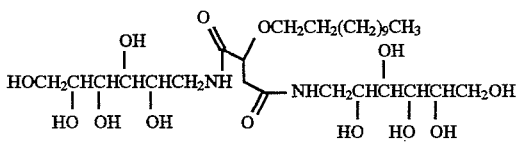

wherein based on formula (II) above:

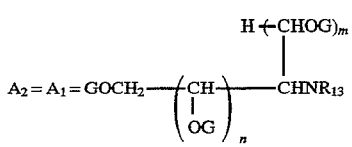

G=hydrogen (H);
$R_9=C_{10}H_{21}$;
$R_{13}$=hydrogen (H);
W=oxygen (O);
Z=$CH_2CH_2$;
c=1;
e=0;
m=0;
and n=4.

Another specific example of a monosaccharide alkyl bis(glyca)succinamide compound of the invention is tetradecyloxytri(oxyethyl) bis (D-gluco)succinamide, also known as tetradecyloxy(triethylene glycol) ether bis(D-gluco)succinamide or as tetradecyloxy(trioxyethylene) bis (D-gluco)succinamide having the formula:

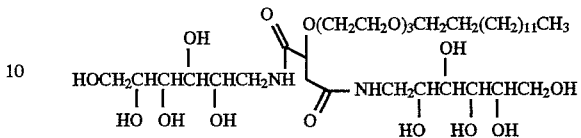

wherein based on formula (II) above:

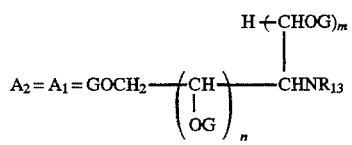

G=hydrogen (H);
$R_9=C_{12}H_{25}$;
$R_{13}$=hydrogen (H);
W=oxygen (O);
X=hydrogen (H);
Y=oxygen (O);
Z=$CH_2CH_2$;
c=1;
d=2;
e=3;
m=0;
and n=4.

Yet another specific example of a monosaccharide alkyl bis(glyca)succinamide compound of the invention is dodecyl bis(D-gluco)succinamide hexaoxyethylene ether, also known as dodecyl bis(D-gluco)succinamide hexaethylene glycol ether or more generally as polyoxyethylene (6) dodecyl bis(D-gluco)succinamide having the formula:

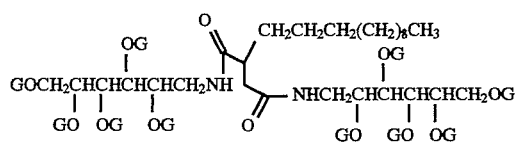

wherein based on formula (II) above:

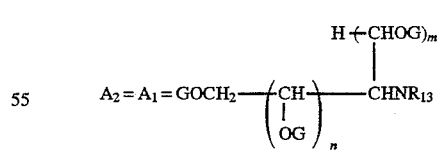

G=hydrogen (H) or $(CH_2CH_2O)_aH$ group;
$R_9=C_9H_{19}$;
$R_{13}$=hydrogen (H);
W=$CH_2$;
Z=$CH_2CH_2$;
a=can vary from about 1 to about 12 for a total average of 6;
c=1;

e=0;
m=0;
and n=4.

A specific example of a monosaccharide alkenyl bis (glyca)succinamide compound of the invention is decenyl bis(D-gluco)succinamide also known as decenyl bis(1-amido-1-deoxy D-glucitol) succinate or decenyl bis(1-amido-1-deoxy D-sorbitol) succinate having the formula:

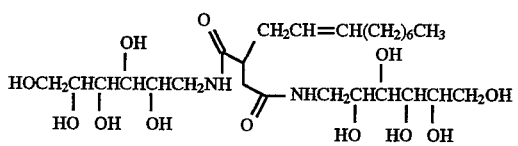

wherein based on formula (II) above:

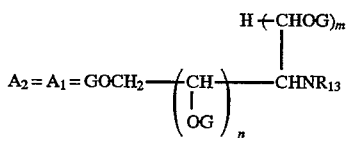

G=hydrogen (H);
$R_9=C_7H_{15}$;
$R_{13}$=hydrogen (H);
$W=CH_2$;
$Z=CH=CH$;
c=1;
e=0;
and n=4.

Another specific example of a monosaccharide alkenyl bis(glyca)succinamide compound of the invention is dodecenyl bis(L-rhamno)succinamide also known as dodecenyl bis(1-amido-1,6-dideoxy L-rhamnitol) succinate or dodecenyl bis(1-amido-1,6-dideoxy L-mannitol) succinate having the formula:

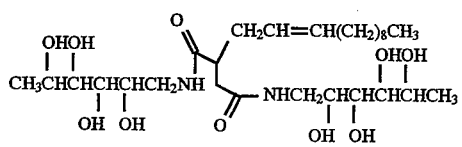

wherein based on formula (II) above:

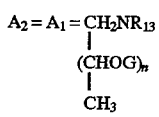

G=hydrogen (H);
$R_9=C_9H_{19}$;
$R_{13}$=hydrogen (H);
$W=CH_2$;
$Z=CH=CH$;
e=0;
and n=4.

A specific example of a cyclic monosaccharide alkenyl bis(glyca)succinamide compound of the invention is decenyl bis(D-sorbitan)succinamide having the formula:

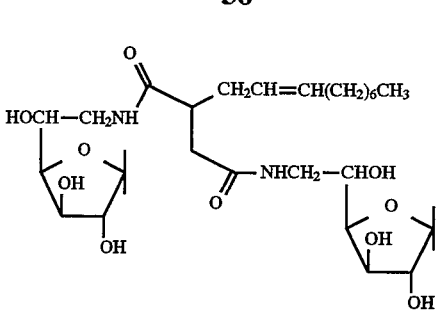

wherein based on formula (II) above:

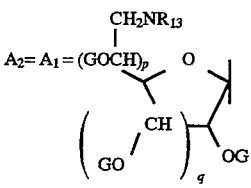

G=hydrogen (H);
$R_9=C_7H_{15}$;
$R_{13}$=hydrogen (H);
$W=CH_2$;
$Z=CH=CH$;
c=1;
e=0;
p=1;
and q=1.

Another specific example of a cyclic monosaccharide alkenyl bis(glyca)succinamide compound of the invention is dodecenyl bis(1-amido-1-deoxy D-fructopyranosyl) succinate having the formula:

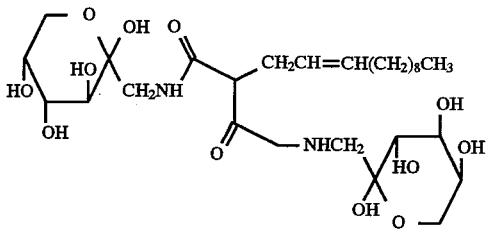

wherein based on formula (II) above:

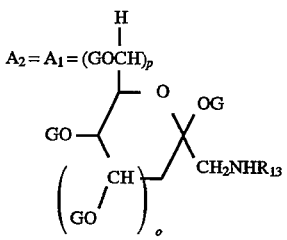

G=hydrogen (H);
$R_9=C_9H_{19}$;
$R_{13}$=hydrogen (H);
$W=CH_2$;
$Z=CH=CH$;
c=1;
e=0;

o=1;

and p=0.

Yet another specific example of a cyclic monosaccharide alkenyl bis(glyca)succinimide compound of the invention is dodecenyl bis(6-amido-6-deoxy α,β-D-methylglucopyranoside) succinate having the formula:

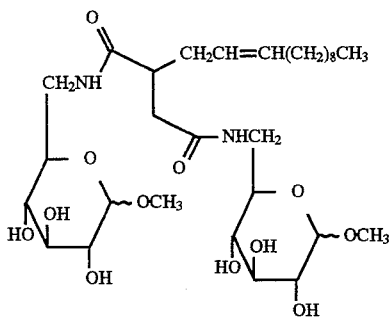

wherein based on formula (II) above:

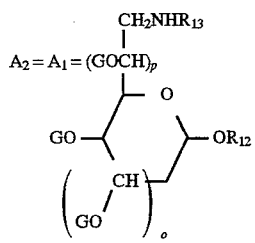

G=hydrogen (H);

$R_9=C_9H_{19}$;

$R_{12}=CH_3$;

$R_{13}$=hydrogen (H);

W=CH$_2$;

Z=CH=CH;

C=1;

e=0;

o=1;

and p=1.

A specific example of a monosaccharide alkyl bis (alkylglyca)succinamide compound of the invention is tetradecyloxydi(oxyethyl) bis(methyl D-gluco)succinamide, also known as tetradecyloxy(diethylene glycol) ether bis (methyl D-gluco)succinamide or as tetradecyloxy (dioxyethylene) bis(methyl D-gluco)succinamide having the formula:

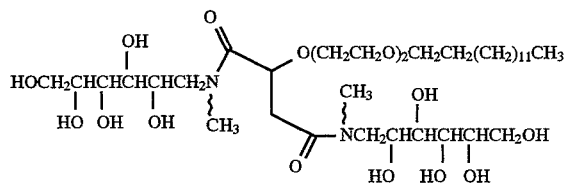

wherein based on formula (II) above:

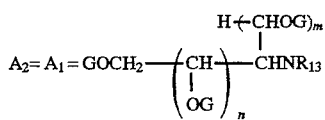

G=hydrogen (H);

$R_9=C_{12}H_{25}$;

$R_{13}=CH_3$;

W=oxygen (O);

X=hydrogen (H);

Y=oxygen (O);

Z=CH$_2$CH$_2$;

c=1;

d=2;

e=2;

m=0;

and n=4.

Another specific example of a monosaccharide alkyl bis(alkylglyca)succinamide compound of the invention is tetradecyl his{methyl D-gluco)succinamide having the formula:

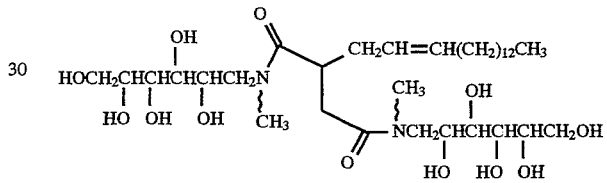

wherein based on formula (II) above:

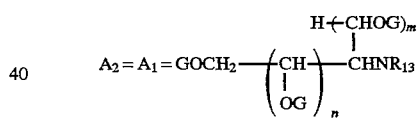

G=hydrogen (H);

$R_9=C_{13}H_{29}$;

$R_{13}=CH_3$;

W=CH$_2$;

Z=CH=CH;

c=1;

e=0;

m=0;

and n=4.

A specific example of a monosaccharide alkenyl bis (alkylglyca)succinamide compound of the invention is hexadecenyl bis(methyl D-gluco)succinamide having the formula:

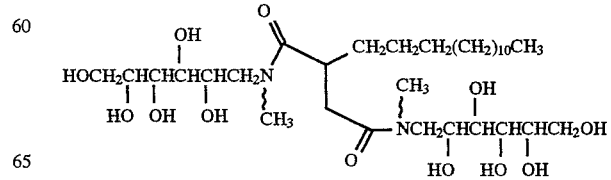

wherein based on formula (II) above:

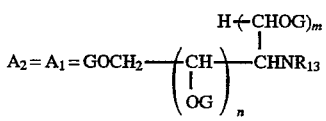

G=hydrogen (H);
$R_9=C_{11}H_{23}$;
$R_{13}=CH_3$;
$W=CH_2$;
$Z=CH=CH$;
c=1;
e=0;
m=0;
and n=4.

A specific example of a mixed monosaccharide alkenyl bis(alkylglyca)succinamide compound of the invention is dodecenyl methyl D-sorbitan(methyl D-gluco)succinamide having the formula:

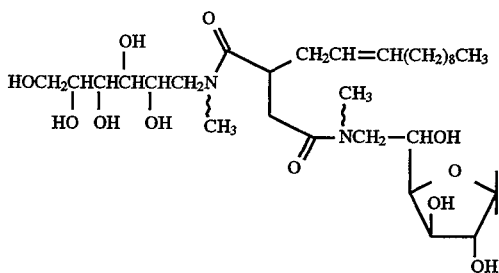

wherein based on formula (II) above:

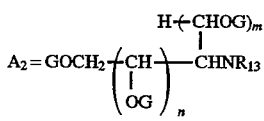

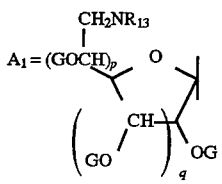

G=hydrogen (H);
$R_9=C_9H_{19}$;
$R_{13}=CH_3$;
$W=CH_2$;
$Z=CH=CH$;
c=1;
e=0;
m=0;
n=4;
p=1;
and q=1

A specific example of a mixed monosaccharide alkenyl alkylglycasuccinamide compound of the invention is decenyl methyl D-glucamidemethylsuccinate having the formula:

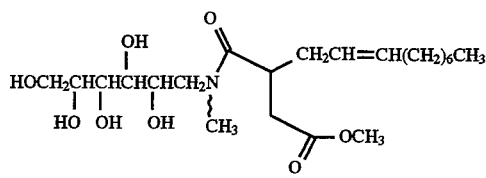

wherein based on formula (II) above:

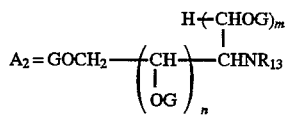

$A_1=OCH_3$
G=hydrogen (H);
$R_9=C_7H_{15}$;
$R_{13}=CH_3$;
$W=CH_2$;
$Z=CH=CH$;
c=1;
e=0;
m=0;
and n=4.

Yet another specific example of a mixed monosaccharide alkenyl alkylglycasuccinamide compound of the invention is tetradecenyl ethanolamide(ethylgluco)succinamide having the formula:

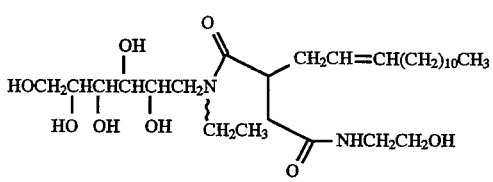

wherein based on formula (II) above:

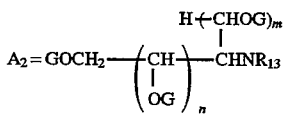

$A_1=HNCH_2CH_2OH$
G=hydrogen (H);
$R_9=C_{11}H_{23}$;
$R_{13}=CH_2CH_3$;
$W=CH_2$;
$Z=CH=CH$;
c=1;
e=0;
m=0;
and n=4.

Yet another specific example of a mixed monosaccharide alkenyl alkylglycasuccinamide compound of the invention is hexadecenyl diglucamide methylsuccinate also known as hexadecenyl disorbitylamide methylsuccinate having the formula:

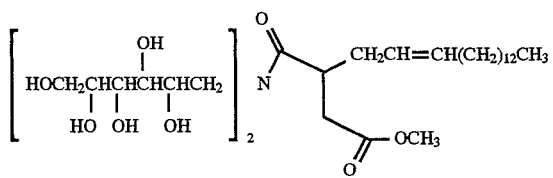

wherein based on formula (II) above:

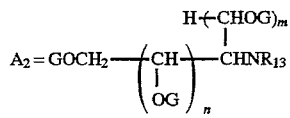

$A_1 = OCH_3$
$G$ = hydrogen (H);
$R_9 = C_{13}H_{27}$;
$R_{13}$ = sorbityl;
$W = CH_2$;
$Z = CH = CH$;
$c = 1$;
$e = 0$;
$m = 0$;
and $n = 4$.

A specific example of a mixed monosaccharide alkyl alkylglycasuccinamide compound of the invention is hexadecenyl ethanolamide(hydroxylethylgluco) succinamide having the formula:

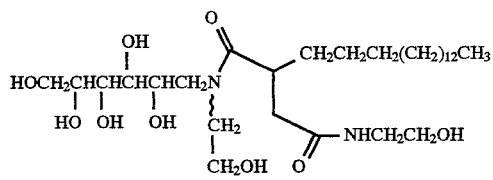

wherein based on formula (II) above:

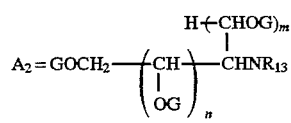

$A_1 = NHCH_2CH_2OH$
$G$ = hydrogen (H);
$R_9 = C_{13}H_{27}$;
$R_{13} = CH_2CH_2OH$
$W = CH_2$;
$Z = CH_2CH_2$;
$c = 1$;
$e = 0$;
$m = 0$;
and $n = 4$.

A specific example of a disaccharide alkyl bis(glyca) succinamide compound of the invention is tetradecyl bis(D-lacto)succinamide having the formula:

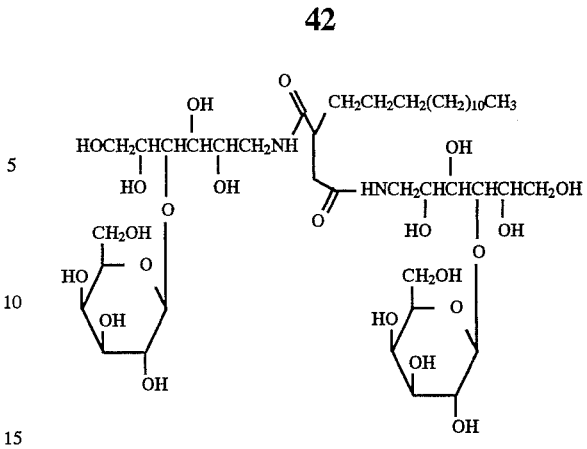

wherein based on formula (II) above:

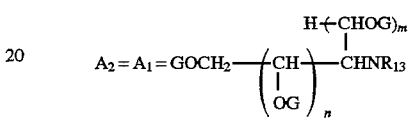

$G$ = hydrogen (H) or galactose;
$R_9 = C_{11}H_{23}$;
$R_{13}$ = hydrogen (H);
$W = CH_2$;
$Z = CH_2CH_2$;
$c = 1$;
$e = 0$;
$m = 0$;
and $n = 4$.

A specific example of a disaccharide alkenyl bis (alkylglyca)succinamide compound of the invention is hexadecenyl bis(methyl D-lacto)succinamide having the formula:

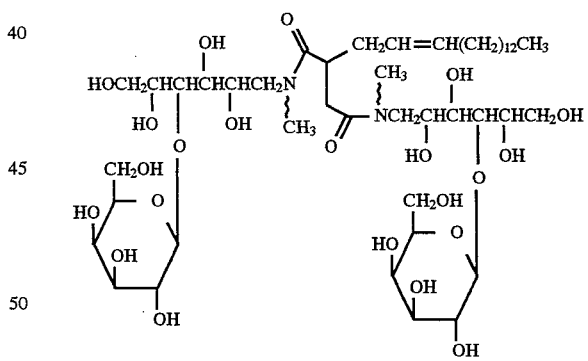

wherein based on formula (II) above:

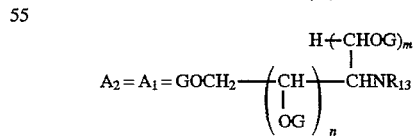

$G$ = hydrogen (H) or galactose;
$R_9 = C_{13}H_{27}$;
$R_{13} = CH_3$;
$W = CH_2$;
$Z = CH = CH$;
$c = 1$;

e=0;
m=0;
and n=4.

A specific example of a mixed disaccharide/monosaccharide alkenyl bis(alkylglyca)succinamide compound of the invention is tetradecenyl methyl D-malto (methyl D-gluco)succinamide having the formula:

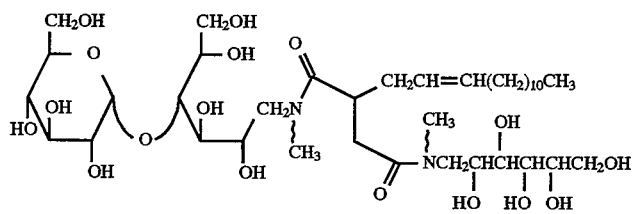

wherein based on formula (H) above:

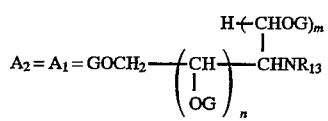

G=hydrogen (H) or glucose;
$R_9=C_{11}H_{23}$;
$R_{13}=CH_3$;
$W=CH_2$;
$Z=CH=CH$;
c=1;
e=0;
m=0;
and n=4.

Yet another specific example of a mixed disaccharide/monosaccharide alkenyl bis(alkylglyca)succinamide compound of the invention is dodecenyl methyl D-malto(methyl D-sorbitan)succinamide having the formula:

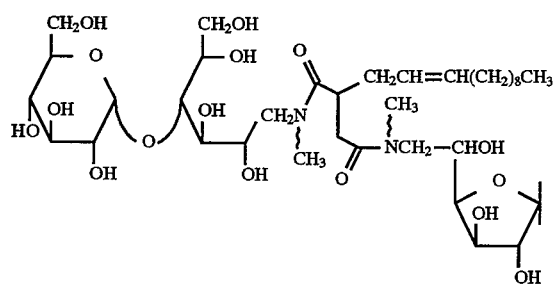

wherein based on formula (II) above:

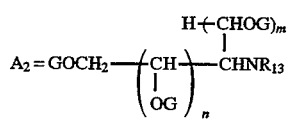

-continued

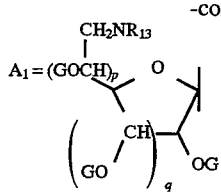

G=hydrogen (H) or glucose;
$R_9=C_9H_{19}$;
$R_{13}=CH_3$;
$W=CH_2$;
$Z=CH=CH$;
c=1;
e=0;
m=0;
p=1;
and q=1.

A specific example of a mixed disaccharide alkenyl alkylglycasuccinamide compound of the invention is dodecenyl methyl d-maltamide methylsuccinate having the formula:

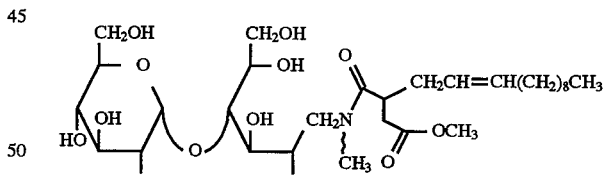

wherein based on formula (II) above:

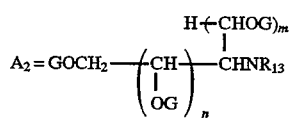

$A_1=OCH_3$
G=hydrogen (H) or glucose;
$R_9=C_9H_{19}$;
$R_{13}=CH_3$;
$W=CH_2$;
$Z=CH=CH$;

c=1;
e=0;
and n=4.

Other examples of compounds of the invention are set forth below:

alkyl and alkenyl bis(D-erythro)succinamide
alkyl and alkenyl bis(D-threo)succinamide
alkyl and alkenyl bis(D-ribo)succinamide
alkyl and alkenyl bis(D-arabino)succinamide
alkyl and alkenyl bis(D-xylo)succinamide
alkyl and alkenyl bis(D-lyxo)succinamide
alkyl and alkenyl bis(D-allo)succinamide
alkyl and alkenyl bis(D-altro)succinamide
alkyl and alkenyl bis(D-ido)succinamide
alkyl and alkenyl bis(D-talo)succinamide
alkyl and alkenyl bis(D-gluco)succinamide
alkyl and alkenyl bis(L-gluco)succinamide
alkyl and alkenyl bis(D-galacto)succinamide
alkyl and alkenyl bis(L-galacto)succinamide
alkyl and alkenyl bis(D-manno)succinamide
alkyl and alkenyl bis(D-gulo)succinamide
alkyl and alkenyl bis(D-fructo)succinamide
alkyl and alkenyl bis(L-fructo)succinamide
alkyl and alkenyl bis(D-sorbo)succinamide
alkyl and alkenyl bis(L-sorbo)succinamide
alkyl and alkenyl bis(D-isomalto)succinamide
alkyl and alkenyl bis(D-isomalt)succinamide
alkyl and alkenyl bis(D-isomaltulo)succinamide
alkyl and alkenyl bis(D-trehalulo)succinamide
alkyl and alkenyl bis(D-ribulo)succinamide
alkyl and alkenyl bis(D-xylulo)succinamide
alkyl and alkenyl bis(D-3-ketosucro)succinamide
alkyl and alkenyl bis(D-leucro)succinamide
alkyl and alkenyl bis(D-lactulo)succinamide
alkyl and alkenyl bis(D-psico)succinamide
alkyl and alkenyl bis(D-rhamno)succinamide
alkyl and alkenyl bis(D-malto)succinamide
alkyl and alkenyl bis(L-malto)succinamide
alkyl and alkenyl bis(D-lacto)succinamide
alkyl and alkenyl bis(L-lacto)succinamide
alkyl and alkenyl bis(D-melibio)succinamide
alkyl and alkenyl bis(D-cellobio)succinamide
alkyl and alkenyl bis(D-cellulo)succinamide
alkyl and alkenyl bis(D-dextro)succinamide
alkyl and alkenyl bis(D-gluco)succinamide monooxyethylene ether
alkyl and alkenyl bis(D-gluco)succinamide dioxyethylene ether
alkyl and alkenyl bis(D-gluco)succinamide trioxyethylene ether
alkyl and alkenyl bis(D-gluco)succinamide pentaoxyethylene ether
alkyl and alkenyl bis(D-gluco)succinamide hexaoxyethylene ether
alkyl and alkenyl bis(D-gluco)suocinamide octaoxyethylene ether
alkyl and alkenyl bis(D-gluco)succinamide nonaoxyethylene ether
alkyl and alkenyl bis(D-gluco)succinamide decaoxyethylene ether
alkyl and alkenyl bis(D-gluco)succinamide trioxypropylene ether
alkyloxy(monooxyethylene) bis(D-gluco)succinamide
alkyloxy(dioxyethylene) bis(D-gluco)succinamide
alkyloxy(trioxyethylene) bis(D-gluco)succinamide
alkyloxy(pentaoxyethylene) bis(D-gluco)succinamide
alkyloxy(heptaoxyethylene) bis(D-gluco)succinamide
alkyloxy(decaoxyethylene) bis(D-gluco)succinamide
alkyloxy(pentaoxypropylene) bis(D-gluco)succinamide
alkyloxyethylamino bis(D-gluco)succinamide
alkyloxyethylamido bis(D-gluco)succinamide Wherein the alkyl or alkenyl group contains from about 1 to about 31 carbon atoms; preferably from about 2 to about 25 carbon atoms, even more preferably from about 3 to about 23 carbon atoms.

If the $R_{13}$ group is an aliphatic radical (saturated or unsaturated hydrocarbon), suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, hepta-decenyl, octadecenyl (oleyl), linoleyl and linolenyl.

If the $R_{13}$ group is interrupted by an aromatic group, the aromatic radical may be for example, benzyl or aniline. Cycloaliphatic radicals are exemplified, but not limited to cyclopentyl and cyclohexyl. Suitable mixed aromatic aliphatic radicals are exemplified by benzylpropyl, phenylethyl, phenoxyethyl and vinylbenzyl.

The alkyl- and alkenyl D-bis(glyca)succinamide compounds of the present invention can also be ethoxylated, propoxylated or butoxylated with ethylene oxide, propylene oxide, butylene oxide or mixtures thereof to give a series of novel polyoxyalkylene sugar surfactants.

The alkyl- and alkenyl D-bis(glyca)succinamide compounds of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The alkyl- and alkenyl D-bis(glyca)succinamide compounds of the present invention can also be phosphorylated with phophorus oxychloride, phosphorous pentoxide, polyphosphoric acid, phosphoric acid, phosphorus trichloride and the like as well as mixtures thereof, to give a series of novel phosphated sugar based esters (mono-, dio, and triesters as well as mixtures thereoff as anionic surfactants.

In a forth embodiment of the invention, a new and improved process for the manufacture of alkyl- and alkenyl bis(glyca)succinamide surfactants is described.

It has been found, in accordance with the present invention, that novel alkyl- and alkenyl bis(glyca) succinamide surfactants may be readily prepared by (Step IB) reacting alkyl- or alkenyl succinic anhydrides with alcohols in the presence of an acid catalyst at elevated temperatures ($\Delta$) to give the corresponding alkyl- or alkenyl succinate which is then (Step IIC) reacted with glycamines (sugar-$NHR_{13}$) in the presence of a base catalyst at elevated temperatures ($\Delta$). The invention can be more readily understood when reference is made to the following general equations (B and C):

Step IB

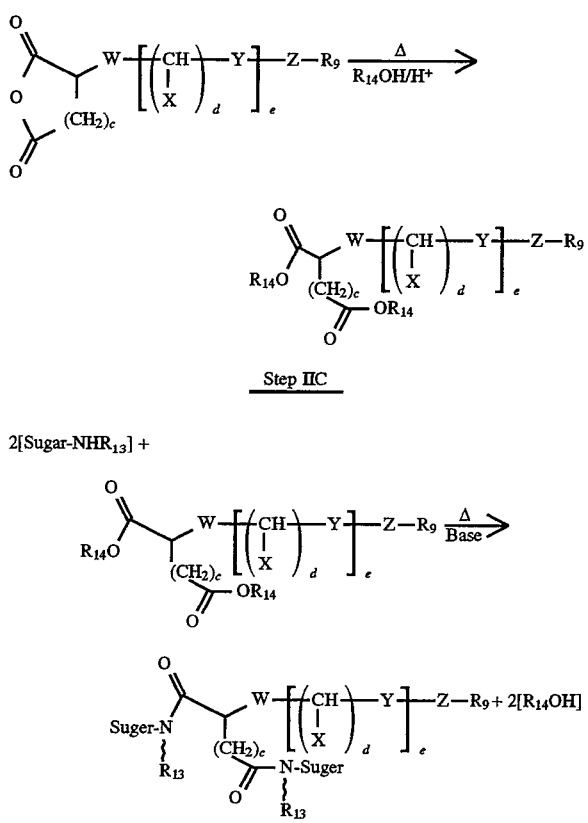

Step IIC

2[Sugar-NHR$_{13}$] +

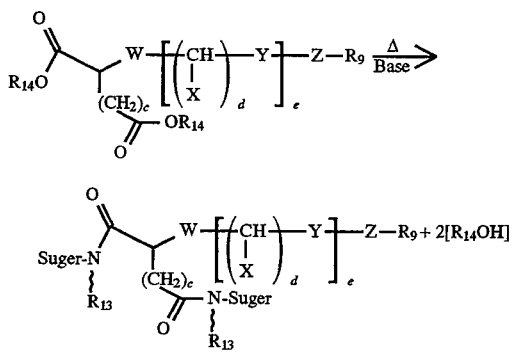

The method is suitable for the manufacture of alkyl- and alkenyl bis(glyca)succinamide compounds wherein W is preferably $CH_2$ or an oxygen atom (O); X is preferably hydrogen (H), or an alkyl group having about 1 to about 2 carbon atoms: Y is preferably a $NR_{10}$, $+N(R_{10})_2$, oxygen (O) group or mixtures thereof: Z is preferably a CH=CH or $CH_2CH_2$ group: $R_9$ is preferably a straight chain saturated hydrocarbon which may be unsubstituted or substituted with an aromatic, cycloaliphatic or mixed aromatic radical comprising from about 2 to about 25 carbon atoms: $R_{13}$ is preferably hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 16 carbon atoms: $R_{14}$ is preferably a straight or branched chain, saturated or unsaturated hydrocarbon radical having about 1 to about 5 carbon atoms: c is preferably 1–3; d is preferably 1–4: and e is preferably 0–25.

The method is especially suitable for the manufacture of alkyl- and alkenyl bis(glyca)succinamide compounds wherein W is more preferably $CH_2$ or an oxygen atom (O); X is more preferably hydrogen (H), or an alkyl group having 1 carbon atom: Y is more preferably an oxygen (O) atom: Z is more preferably a CH=CH or $CH_2CH_2$ group: $R_9$ is more preferably a straight chain saturated hydrocarbon which may be unsubstituted or substituted with an aromatic, cycloaliphatic or mixed aromatic radical comprising from about 3 to about 23 carbon atoms: $R_{13}$ is more preferably hydrogen (H), a straight or branched chain saturated or unsaturated hydrocarbon which may be unsubstituted or substituted with a hydroxyl, or polyhydroxyl group having about 1 to about 6 carbon atoms; $R_{14}$ is more preferably a straight or branched chain, saturated or unsaturated hydro- carbon radical having about 1 to about 5 carbon atoms: c is more preferably 1–2: d is more preferably 1–4: and e is more preferably 0–15.

Examples of glycamines (1-amino-1-deoxyalditols, 2-amino-2-deoxyketitols, 1-alkylamino-1-deoxyalditols etc.) suitable for this method include those of the formula:

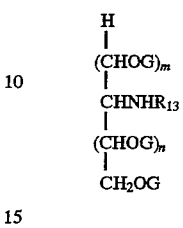

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to glyceramine, erythramine, threamine, ribamine, arabinamine, xylamine, lyxamine, aliamine, altramine, glucamine (1-amino-1-deoxyglucitol), mannamine, gulamine, idamine, galactamine, talamine, glucoheptamine (1-amino-1-deoxyglucoheptitol), 1-amino-1-deoxyglyceroglucoheptitol, 1-amino-1-deoxyglycergalactoheptitol, 1-amino-1-deoxyglyceromannoheptitol, 1,3-dihydroxy-2-propylamine, erythrulamine (threulamine or glycerotetrulamine), ribulamine (erythropentulamine), xylulamine (threopentulamine), psicamine, fructamine (levulamine or 2-amino-2-deoxyfructitol), sorbamine (2-amino-2-deoxysorbitol), tagatamine, 2-amino-2-deoxyalloheptulitol, 3-amino-3-deoxyaltro-3-heptulitol, 2-amino-2-deoxymannoheptulitol, 2-amino-2-deoxysedoheptulitol, 2-amino-2-deoxytaloheptulitol, 2-amino-2-deoxyglycerogalactooctulitol, 2-amino-2-deoxyglyceromannooctulitol, 2-amino-2-deoxyerythrogalactononulitol, 2-amino-2-deoxyerythroglucocononulitol, lactamine [galactopyranosyl-β-(1-4)-1-amino-1-deoxyglucitol], maltamine [glucopyranosyl-α-(1-4)-1-amino-1-deoxyglucitol], isomaltamine-A [glucopyranosyl-α-(1-6)-1-amino-1-deoxyglucitol], isomaltamine-B [glucopyranosyl-α-(1-6)-2-amino-2-deoxyfructitol], isomaltulamine [palatinamine or glucopyranosyl-α-(1-6)-2-amino-2-deoxyfructitol], cellobiamine [glucopyranosyl-β-(1-4)-1-amino-1-deoxyglucitol], leucramine [glucopyranosyl-α-(1-5)-2-amino-2-deoxyfructitol], gentiobiamine [glucopyranosyl-β-(1-6)-1-amino-1-deoxyglucitol], laminarbiamine [glucopyranosyl-β-(1-3)-1-amino-1-deoxyglucitol], xylobiamine [xylopyranosyl-β-(1-4)-1-amino-1-deoxyxylitol], inulobiamine [fructopyranosyl-β-(2-1)-2-amino-2-deoxyfructitol], mannobiamine [mannopyranosyl-[B-(1-4)-1-amino-1-deoxymannitol], 3-ketopalatinamine [3-ketoglucopyranosyl-α-(1-6)-2-amino-2-deoxyfructitol], arabinofuranosyl-α-(1-3)-1-amino-1-deoxyarabinitol, galactopyranosyl-α-(1-3)-1-amino-1-deoxygalactitol, maltotriamine [glucopyranosyl-α-(1-4)-glucopyranosyl-α-(1-4)-1-amino-1-deoxyglucitol], cellotriamine [glucopyranosyl-β-(1-4)-glucopyranosyl-β-(1-4)-1-amino-1-deoxyglucitol], panosamine [glucopyranosyl-α-(1-6)-glucopyranosyl-α-(1-4)-1-amino-1-deoxyglucitol], maltoheptamine [glucopyranosyl-α-(1-4)-{glucopyranosyl-α-(1-4)}$_5$-1-amino-1-deoxyglucitol], starchamine, dextramine, cellulamine, 2-amino-2-deoxyglucitol (2-amino-2-deoxysorbitol), 3-amino-3-deoxyglucitol, 4-amino-4-deoxyglucitol, 6-amino-6-deoxyglucitol, 3-amino-3-deoxyribitol, 2-amino-2-deoxygalactitol, 2-amino-2-deoxymannitol, 2-amino-2-deoxyallitol, 5-amino-5-deoxyaltritol, 6-amino-6-deoxyerythrogalactooctitol, methylglucamine (1-methylamine-1-deoxyglucitol or 1-methylamine-1-deoxysorbitol), ethylglucamine, propylglucamine, butylglucamine, hydroxyethylglucamine, coconutglucamine, disorbitylamine, methyllactamine [galactopyranosyl-β-(1-4)-1-methylamino-1-deoxyglucitol], methylmaltamine [glucopyranosyl-α-(1-4)-1-methylamino-1-deoxyglucitol], ethyllactamine, propyllactamine, butyllactamine, hydroxyethyllactamine, coconutlactamine, ethylmaltamine, propylmaltamine, butylmaltamine, coconutmaltamine, pentylmaltamine, methyloxypropylglucamine, methyloxy-propyllactamine, methyloxypropylmaltamine and $C_2$–$C_{18}$ oxypropylglucamine.

Examples of other glycamines (1-amino-1,6-dideoxyalditols and 1-alkylamino-1,6-dideoxyalditols) suitable for this method include those of the formula:

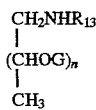

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 1-amino-1,6-dideoxygluicitol, 1-amino-1,6-dideoxyaltritol, 1-amino-1,6-dideoxyglucitol, 1-amino-1,6-dideoxygulitol, 1-amino-1,6-di-deoxytalitol, 1-amino-1,6-dideoxyfucitol, 1-amino-1,6-dideoxyrhamnitol, 1-methylamino-1,6-dideoxyrhamnitol, 1-ethylamino-1,6-dideoxyrhamnitol, 1-coconutamino-1,6-dideoxyrhamnitol, 1-methyloxypropylamino-1,6-dideoxyrhamnitol.

Still other examples of glycamines (1-amino-1-deoxyketoses and 1-alkylamino-1-deoxyketoses) suitable for this method include those of the formula:

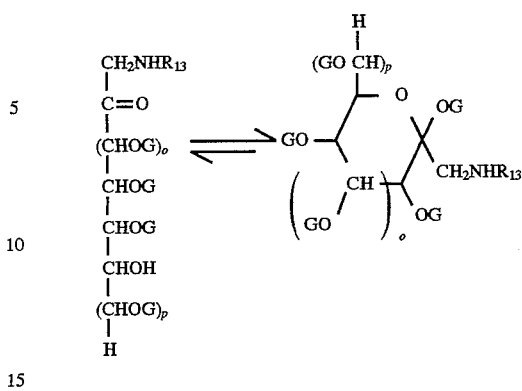

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. These glycamines are described as Amadori rearrangement products and methods for preparing such are disclosed in Methods in Carbohydr. Chem. 2, 99, (1963) to Hodge and Fisher which is incorporated herein by reference. Illustrative of this class include, but are not limited to 1-amino-1-deoxyribulose, 1-amino-1-deoxyxylulose, 1-amino-1-deoxypsicose, 1-amino-1-deoxyfructose (1-amino-1-deoxylevulose), 1-amino-1-deoxyfructose hydrochloride, 1-amino-1-deoxyfructose acetate salt, 1-amino-1-deoxyfructose oxalate salt, 1-amino-1-deoxysorbose, 1-amino-1-deoxytagatose, 1-amino-1-deoxyalloheptulose, 1-amino-1-deoxymannoheptulose, 1-amino-1-deoxysedoheptulose, 1-amino-1-deoxytaloheptulose, 1-amino-1-deoxyglycerogalactooctulose, 1-amino-1-deoxyglyceromannooctulose, 1-amino-1-deoxyerythrogalactononulose, galactopyranosy-β-(1,4)-1-amino-1-deoxyfructose, glucopyranosyl-α-(1-4)-1-amino-1-deoxyfructose, glucopyranosyl-β-(1-4)-glucopyranosyl-β-(1-4)-1-amino-1-deoxyfructose, glucopyranosyl-α-(1-4)-{glucopyranosyl-α-(1-4)}$_4$-1-amino-1-deoxyfructose, 1-methylamino-1-deoxyfructose hydrochloride, 1-ethylamino-1-deoxyfructose acetate salt, 1-propylamino-1-deoxyfructose oxalate salt, 1-hydroxypropylamino-1-deoxyfructose 1-coconutamino-1-deoxyfructose, 1-tallowamino-1-deoxyfructose, 1-$C_1$–$C_{18}$ alkyloxypropylamino-1-deoxyfructose, 1-$C_1$–$C_{18}$ alkyloxypropylaminopropylamino-1-deoxyfructose, 1-methylamino-1-deoxyfructose, 1-ethylamino-1-deoxyfructose, 1-propylamino-1-deoxyfructose, 1-hexylamino-1-deoxyfructose and 1-octylamino-1-deoxyfructose.

Still other examples of glycamines (1-amino-1-deoxyaldoses, 2-amino-2-deoxyketoses, 1-alkylamino-1-deoxyaldoses and 2-alkylamino-2-deoxyketoses) suitable for this method include those of the formula:

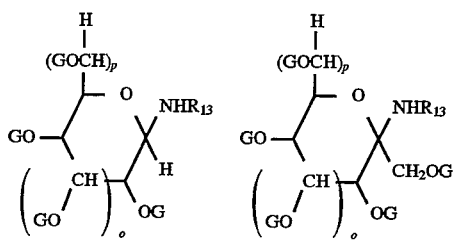
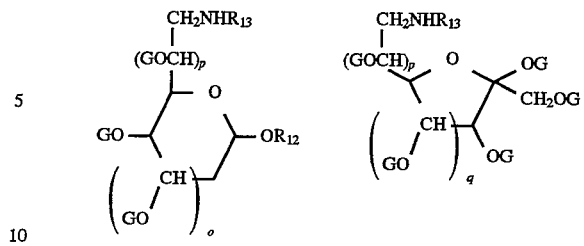

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 1-amino-1-deoxyribose, 1-amino-1-deoxyxylose, 1-amino-1-deoxyglucose, 1-amino-1-deoxymannose, 1-amino-1-deoxygulose, 1-amino-1-deoxyidose, 1-amino-1-deoxygalactose, 1-amino-1-deoxyglucoheptose, 1-amino-1-deoxyglyceroglucoheptose, 2-amino-2-deoxyfrucose, 2-amino-2-deoxysorbose, 1-amino-1-deoxylactose [galactopyranosyl-β-(1-4)-1-amino-1-deoxyglucose], 1-amino-1-deoxymaltose [glucopyranosyl-α-(1-4)-1-amino-1-deoxyglucose], 1-amino-1-deoxymaltotriose [glucopyranosyl-α-(1-4)-glucopyranosyl-α-(1-4)-1-amino-1-deoxyglucose], 1-amino-1-deoxymaltoheptose [glucopyranosyl-α-(1-4)-{glucopyranosyl-α-(1-4)}$_5$-1-amino-1-deoxyglucose], 1-methylamino-1-deoxyglucose, 1-ethylamino-1-deoxyglucose, 1-propylamino-1-deoxyglucose, 1-butylamino-1-deoxyglucose, 1-coconutamino-1-deoxyglucose, 1-tallowamino-1-deoxyglucose, 1-methyloxypropyl-amino-1-deoxyglucose, 1-$C_2$–$C_{18}$ alkyloxypropylamino-1-deoxyglucose, 1-methylamino-1-deoxylactose, 1-ethylamino-1-deoxylactose, 1-propylamino-1-deoxylactose, 1-butylamino-1-deoxylactose, 1-coconutamino-1-deoxylactose, 1-methylamino-1-deoxymaltose, 1-ethylamino-1-deoxymaltose, 1-propylamino-1-deoxymaltose, 1-hydroxyethylamino-1-deoxymaltose, 1-methyloxypropylamino-1-deoxymaltose, 1-coconutamino-1-deoxymaltose, 1-methylamino-1-deoxymaltotriose, 1-coconutamino-1-deoxymaltotriose and 1-methylamino-1-deoxymaltopentiose.

Still other examples of glycamines (6-amino-6-deoxyaldoses, 6-amino-6-deoxyketoses, 6-amino-6-deoxyglycosides, 6-alkylamino-6-deoxyaldoses, 6-alkylamino-6-deoxyketoses, 6-alkylamino-6-deoxyglycosides, etc.) suitable for this method include those of the formula:

wherein G is hydrogen (H), a $(CH_2CH_2O)_aH$ or $(CH_2CHCH_3O)_bH$ group, a mono-, di-, oligo- or polysaccharide or mixtures thereof; $R_{12}$ is hydrogen (H), or an alkyl, alkenyl or hydroxyalkyl group having about 1 to about 5 carbon atoms; a and b are each from about 0 to about 35 and the sum of a and b are from about 0 to about 35; o is from about 0 to about 2, p is from about 0 to about 4 and q is from about 0 to about 3; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 5-amino-5-deoxyribose, 5-amino-5-deoxyxylose, 6-amino-6-deoxyallose, 6-amino-6-deoxyaltrose, 6-amino-6-deoxyglucose, 6-amino-6-deoxyglucose hydrochloride, 6-amino-6-deoxymethylglucoside, 6-amino-6-deoxyethylglucoside, 6-amino-6-deoxymannose, 6-amino-6-deoxygulose, 6-amino-6-deoxyidose, 6-amino-6-deoxygalactose, 6-amino-6-deoxytalose, 7-amino-7-deoxyglucoheptose, 7-amino-7-deoxyglyceroglucoheptose, 7-amino-7-deoxyglycergalactoheptose, 7-amino-7-deoxyglyceromannoheptose, 6-amino-6-deoxyfructose, 7-amino-7-deoxyalloheptulose, 7-amino-7-deoxymannoheptulose, 7-amino-7-deoxysedoheptulose, 7-amino-7-deoxytaloheptulose, 8-amino-8-deoxyglycerogalactooctulose, 8-amino-8-deoxyglyceromannooctulose, 9-amino-9-deoxyerythrogalactononulose, 9-amino-9-deoxyerythroglucononulose, galactopyranosyl-β-(1-4)-6-amino-6-deoxyglucose, 6-amino-6-deoxygalactose-β-(1-4)-glucopyranose, 6-amino-6-deoxygalactose-β-(1-4)-6-amino-6-deoxyglucose, glucopyranosyl-α-(1-4)-6-amino-6-deoxyglucose, 6-amino-6-deoxyglucose-α-(1-4)-glucopyranose, 1-amino-1-deoxy-β-fructofuranosyl-α-glucopyranoside, 6-amino-6-deoxy-β-fructofuranosyl-α-glucopyranoside, β-fructofuranosyl-α-6-amino-6-deoxyglucopyranoside and glucopyranosyl-α-(1-4)-{glucopyranosyl-α-(1-4)}$_5$-6-amino-6-deoxyglucose, 6-methylamino-6-deoxyglucose, 6-ethylamino-6-deoxyglucose, 6-propylamino-6-deoxyglucose, 6-butylamino-6-deoxyglucose, 6-coconutamino-6-deoxyglucose, 6-hydroxyethylamino-6-deoxyglucose, 6-methyloxypropylamino-6-deoxyglucose, 6-methylamino-6-deoxymethylglucoside, 6-ethylamino-6-deoxyethylglucoside, 6-propylamino-6-deoxycoconutglucoside, 6-butylamino-6-deoxymethylglucoside, 6-coconutamino-6-deoxyglucoside, 6-hydroxyethylamino-6-deoxypropylglucoside and 6-methyloxypropylamino-6-deoxymethylglucoside.

Many additional examples of glycamines that are useful in the present invention are described in "Carbohydrates" edited by Collins, published by Chapman and Hall Ltd., (1987) and "The Carbohydrates, Chemistry and Biochemistry" edited by Pigman and Horton, 2nd Edition, Volumes IA, IIA, IB and IIB, published by Academic Press Inc., (1972): all of which are incorporated herein by reference.

Of the above described glycamines, those of the following formulas are most highly preferred:

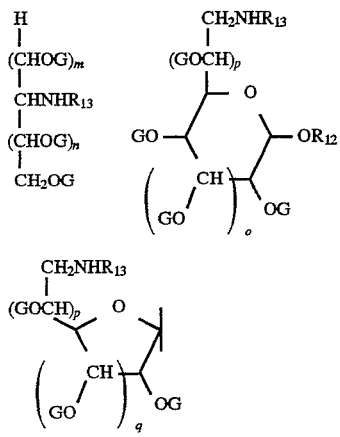

wherein G is hydrogen (H) or a monosaccharide; $R_{12}$ is hydrogen (H) or an alkyl, alkenyl or hydroxyalkyl group having from about 1 to about 4 carbon atoms; $R_{13}$ is hydrogen (H), a straight or branched chain saturated or unsaturated hydrocarbon which may be unsubstituted or substituted with a hydroxyl, polyhydroxyl radical having about 1 to about 6 carbon atoms; m=0; n=1–4; o=0–1; p=0–1 and q=1.

Examples of suitable alkyl and alkenyl succinic anhydrides, alkyl and alkenyl succinic acids (dicarboxylic acids) and alkyl and alkenyl succinic acid esters are those as described above.

It has been found, in accordance with the present invention, that novel alkyl- and alkenyl bis(glyca) succinamide surfactants may be readily prepared by (Step IB) reacting alkyl- or alkenyl succinic anhydrides with alcohols in the presence of an acid catalyst at elevated temperatures to give the corresponding alkyl- or alkenyl succinate which is then (Step IIC) reacted with glycamines (sugar-$NHR_{13}$) in the presence of a base catalyst at elevated temperatures.

Description of the Essential Process Parameters of Step IB

Within the first step of the process of the invention, it is desirable to use water-free reaction components, although small amounts of water (from about 1% to about 2% by weight) can be tolerated. Also, within the first step of the process of the invention, the alcohol can be added progressively to the anhydride, or the anhydride can be added progressively to the alcohol, preferably however, both reagents are added in full amount at the beginning of the reaction. The alcohol is preferably used in molar excess relative to the anhydride. The molar ratio of alcohol to alkyl- or alkylene anhydride is from about 150:1 to about 2:1, preferably from about 80:1 to about 3:1, more preferably from about 40:1 to about 4:1.

The succinate is preferably in liquid to gel form, however crystalline, granular, solid, flake or paste form can be used as well.

The reaction can be performed at or below room temperature, however shorter reaction times can be achieved at elevated temperature and is usually preferred. Favorable reaction temperatures are from about 20° C. to about 160° C., preferably from about 30° C. to about 140° C., most preferably from about 40° C. to about the boiling point of the alcohol (reflux) that is used for esterification of the anhydride. The reaction can be carried out under reduced pressure to assist in the removal of solvent or alcohol, however, it is preferably carried out at atmospheric pressure and under an inert gas blanket such as nitrogen, argon or helium, most preferably it is carried out at atmospheric pressure.

The catalyst used to accelerate the rate of the reaction is generally classified as an organic or inorganic acid. Examples of suitable acid catalysts useful in the present method are those as described above.

The acid catalyst can be added at any time during the reaction, however, it is preferably added at the beginning of the reaction and in full mount. The molar ratio of anhydride to acid catalyst is from about 700:1 to about 1:1, preferably from about 350:1 to about 25:1, most preferably from about 250:1 to about 45:1.

The substrates are reacted with intensive stirring for several hours, preferably from about 24 hours to about 0.5 hour, more preferably from about 15 hours to about 1 hour, most preferably when the reaction is deemed complete and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), gas chromatography mass spectrometry (GC MS) or high pressure liquid chromatography (HPLC). The catalyst is then neutralized with base whose mount is sufficient to provide a pH in the rage of about 6 to about 11, preferably from about 7 to about 10, most preferably greater than 9. Neutralization may be done at temperatures from about 0° C. to about 35° C.

Excess alcohol is optionally removed by known procedures such as simple distillation, vacuum distillation or rotaevaporation, or it may be allowed to remain with the finished product and used as a solvent for Step IIC.

Description of the Essential Process Parameters of Step IIC

Within the second step of the process of the invention, it is desirable to use nearly water-free reaction components, however this is not an essential condition. Also, within the second step of the process of the invention, the glycamine can be added progressively to the succinate, or the succinate can be added progressively to the glycamine, or both reagents can be added at the beginning of the reaction, preferably however, the glycamine is added in full amount to the succinate. The glycamine can be used in molar excess relative to the succinate, or the succinate can be used in molar excess relative to the glycamine, preferably however, as seen in Examples 23 through 27, the glycamine is used in molar excess relative to the succinate. The molar ratio of glycamine to alkyl- or alkenyl succinate is from about 3:1 to about 1.5:1, preferably from about 2.5:1 to about 1.7:1, more preferably from about 2.1:1 to about 1.9:1.

The glycamine is preferably in crystalline to granular form, however solid, flake, paste, gel or liquid forms can be used as well.

The reaction may be performed at or below room temperature, however shorter reaction times can be achieved at elevated temperature and is usually preferred. Favorable reaction temperatures are from about 20° C. to about 250° C., preferably from about 30° C. to about 220° C., most preferably from about 40° C. to about 200° C. The reaction can be carried out under reduced pressure to assist in the removal of solvent or alcohol, however, it is preferably carried out at atmospheric pressure and under an inert gas blanket such as nitrogen, argon or helium, most preferably it is carried out at atmospheric pressure.

The catalyst used to accelerate the rate of the reaction is generally classified as an organic or inorganic base. Examples of suitable base catalysts useful in the present method are those as described above.

The base catalyst can be added at any time during the reaction, however, it is preferably added at the beginning of the reaction and in full mount. The molar ratio of glycamine to base catalyst is from about 500:1 to about 1:1, preferably from about 250:1 to about 5:1, most preferably from about 150:1 to about 10:1.

The substrates are reacted with intensive stirring for several hours, preferably from about 0.5 hour to about 20 hours, more preferably from about 1 hour to about 15 hours, most preferably when the reaction is deemed complete and is verified by an analytical technique such as thin layer chromatography (TLC), infrared spectroscopy (IR), proton nuclear magnet resonance (HI NMR), carbon 13 nuclear magnet resonance (C13 NMR), direct chemical ionization mass spectrometry (DCI MS), fast atom bombardment mass spectrometry (FAB MS) or high pressure liquid chromatography (HPLC).

In general, an organic solvent can be used to perform the reaction (Step IB and Step IIC) of the present invention, however, these materials are usually not necessary and are therefore not preferred. However, when an organic solvent is used, the quantity of solvent should be sufficient to dissolve the carbohydrate and succinate, but otherwise this is not an essential condition. An organic solvent may become necessary when heat sensitive carbohydrates are used (e.g., certain Z-deoxy-Z-aminoaldoses or ketoses). Typical levels of solvent used are from about 5% to about 95%, preferably from about 15% to about 75%, most preferably from about 30% to about 50% by weight of the total reaction mixture. Preferably the solvent is removed (after the reaction is complete) by known procedures such as simple distillation, vacuum distillation or rotaevaporation. When water is added, it is generally used as a diluent making the product a pureable liquid. Typical levels of water used as a reaction solvent or diluent are from about 5% to about 95%, preferably from about 15% to about 65%, most preferably from about 25% to about 50% by weight of the total reaction mixture.

In general, the nonionic alkyl- and alkenyl bis(glyca) succinamide surfactants of the present invention are usually isolated as solids or semisolids, however, when syrups are obtained, crystallization may be enhanced by the addition of an organic solvent. The resulting product is subsequently filtered, washed with an organic solvent and air or vacuum dried.

Optionally, further purification of (solid) alkyl- and alkenyl bis(glyca)succinamide surfactants can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Examples of typical reaction solvents, crystallization solvents and recrystallization solvents that useful in the present method are those as described above.

When the reaction is complete, the base catalyst may be optionally neutralized with an organic or inorganic acid. Preferred neutralizing acids include hydrochloric acid, oxalic acid, tartaric acid, citric acid, formic acid, lactic acid, lauric acid, dodecenyl succinic acid, dodecylbenzenesulfonic acid and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof, at about 0° C. to about 35° C.

Bleaching is sometimes required in either Step IB or Step IIC of the process, but not always necessary, since compounds of the invention are usually of good color. Examples of suitable bleaching agents useful in the present method are those as described above. Typical levels of bleaching agent are from about 0.01% to about 10%, preferably from about 0.02% to about 7%, even more preferably from about 0.03% to about 5% by weight of the total reaction mixture.

Color improvement may also be carried out in either Step IB or Step IIC of the process by using reducing agents. Examples of suitable reducing agents useful in the present method are those as described above. Typical levels of reducing agent are from about 0.01% to about 12%, preferably from about 0.02% to about 9%, even more preferably from about 0.03% to about 7% by weight of the total reaction mixture.

The glycasuccinimide compounds prepared by the method of the invention are generally isolated as crystalline solids in good yield, good purity and desirable color.

EXAMPLES

In order to more fully illustrate the nature of the invention and the manner of practicing the same, the following examples are presented. These Examples are given solely for the purpose of illustration and are not to be construed as being limiting to the present invention since many variations are possible without departing from the spirit and scope of the invention. For example, the following pseudo-glycamines are considered to be equivalent to the glycamines of the invention and can be easily used in the process of the invention to form new nonionic glycasuccinamide surfactants. Examples of pseudo-glycamines include, but are not limited to 1-amino-2-propanol, DL-2-amino-1-propanol, 2-amino-2-methylpropanol, 3-amino-1 -propanol, 2-amino-1-butanol, 4-amino-1-butanol, 5-amino-1-pentanol, monoethanolamine, diethanolamine, 2-amino-2-methyl-1,3-propanol, 2-amino-2-ethyl-1,3-propanediol [1,1-bis(hydroxymethyl)propylamine], 3-amino-1,2-propanediol [1,2-dihydroxy-1-propylamine], 3-methylamino-1,2-propanediol tris(hydroxyethyl)amine [2-amino-2-(hydroxymethyl)-1,3-propanediol], tris(hydroxymethyl) aminomethane and the like.

Example 1 (Comparative)

Preparation of Dodecenyl Sorbitan Succinate Ester

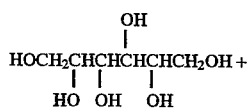

-continued

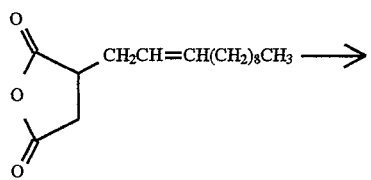

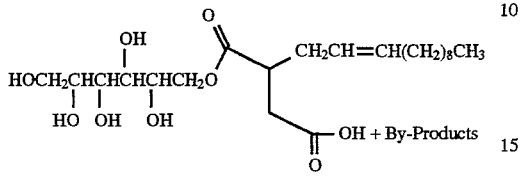
+ By-Products

A 100 ml four necked round bottom flask equipped with a mechanical stirrer, thermometer, nitrogen inlet and short path distillation head was charged with D-sorbitol (15.0 g, $8.23 \times 10^{-2}$ mole, 99.9+% pure), distilled dodecenylsuccinic anhydride (21.9 g, $8.23 \times 10^{-2}$ mole) and sodium methoxide (0.07 g, $1.30 \times 10^{-3}$ mole). The reaction mixture was heated to 150° C. for 4 hours under a mild nitrogen blanket giving 33.6 g (91.5% yield) of dodecenyl D-sorbitan succinate ester as a viscous dark amber syrup.

| IR Analysis (cm − 1, Nujol) | |
|---|---|
| cm − 1 | Functional Group |
| 3700–3100 | Hydrogen Bonded O—H Stretch |
| 3000–2840 | C—H and =C—H Stretch |
| 1745–1705 | C=O Stretch (Ester and Acid) |
| 1450 and 1375 | $CH_3$ Bend |
| 1465 | $CH_2$ Bend |
| 1300–975 | C—O Stretch and =C—H Out of Plane Bend |
| 720 | $CH_2$ Rock |

| C13 NMR Analysis (δ, ppm, DMSO D6/TMS) | |
|---|---|
| (δ) | Carbon Type |
| 14.0 | $\underline{C}H_3$ |
| 22.4 | $\underline{C}H_2CH_3$ |
| 28.8–29.3 | $(\underline{C}H_2)_6$ |
| 31.2 | $\underline{C}H_2CH_2CH_3$ |
| 31.6 | $>\underline{C}H_2CH=CH$ |
| 34.5–34.8 | Succinate Ring ($\underline{C}H\underline{C}H_2$) |
| 59.5–88.3 | Sugar Carbons |
| 126.2–125.8 | $CH=\underline{C}H$ (Cis and Trans) |
| 133.3–132.0 | $\underline{C}H=CH$ (Cis and Trans) |
| 176.6–171.0 | $\underline{C}OOCH_2$, $\underline{C}OOCH$, $\underline{C}OOH$ |

δ = Chemical Shift, DMSO D6/TMS = Dimethylsulfoxide/Tetramethylsilane

| H1 NMR Analysis (δ, ppm, DMSO D6/TMS) | |
|---|---|
| (δ) | Proton Type |
| 0.9 t | $CH_3$ |
| 1.2 s | $(C\underline{H}_2)_7$, $>C\underline{H}_2CH=CH$ |
| 2.0–1.8 bd | $COOC\underline{H}_2$, $COOC\underline{H}$, $CH=CHC\underline{H}_2(CH_2)_7$ |
| 2.1–2.9 bm | Succinate Ring ($C\underline{H}C\underline{H}_2$) |
| 3.3–4.4 bm | Sugar Protons |
| 4.6–4.8 bm | Sugar Protons |
| 4.9–5.1 m | Sugar Protons |
| 5.2–5.6 bm | $C\underline{H}=C\underline{H}$ (Cis and Trans) | s = singlet, bd = broad doublet, t = triplet, m = multiplet and bm = broad multiplet

| DCI MS Analysis (NH3), Heating Rate = 150 mA/Min. 1.2 μg in Methanol | | |
|---|---|---|
| m/e | Compound | Ion |
| 146.0 | D-Isosorbide + $NH_4+$ | $(L + 18)+$ |
| 164.0 | D-Sorbitan + $NH_4+$ | $(M + 18)+$ |
| 284.1 | Dodecenyl Succinic Anhydride + $NH_4+$ | $(N + 18)+$ |
| 302.0 | Dodecenyl Succinic Acid + $NH_4+$ | $(P + 18)+$ |
| 430.1 | Dodecenyl D-Isosorbide Succinate + $NH_4+$ | $(Q + 18)+$ |
| 448.1 | Dodecenyl D-Sorbitan Succinate + $NH_4+$ | $(R + 18)+$ |
| 558.4 | Dodecenyl Diisosorbide Succinate + $NH_4+$ | $(S + 18)+$ |
| 576.3 | Dodecenyl D-Isosorbide Sorbitan Succinate + $NH_4+$ | $(T + 18)+$ |
| 594.2 | Dodecenyl D-Disorbitan Succinate + $NH_4+$ | $(U + 18)+$ |
| 696.4 | Didodecenyl D-Isosorbide Disuccinate + $NH_4+$ | $(V + 18)+$ |
| 714.4 | Didodecenyl D-Sorbitan Disuccinate + $NH_4+$ | $(W + 18)+$ |

| | | |
|---|---|---|
| 824.0 | Didodecenyl D-Diisorbide Disuccinate + NH$_4$+ | (X + 18)+ |
| 842.4 | Didodecenyl Isosorbide Sorbitan Disuccinate + NH$_4$+ | (Y + 18)+ |
| 860.0 | Didodecenyl Disorbitan Disuccinate + NH$_4$+ | (Z + 18)+ |
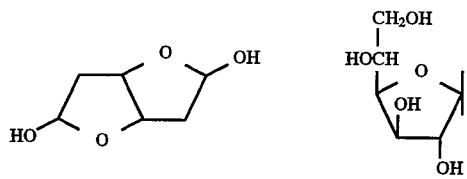
L = 128.0                M = 146.0
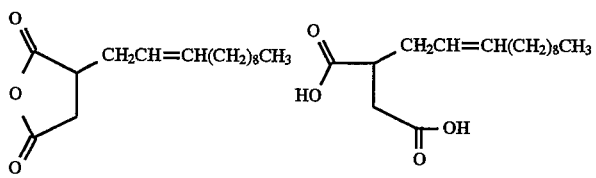
N = 266.1        P = 284.0
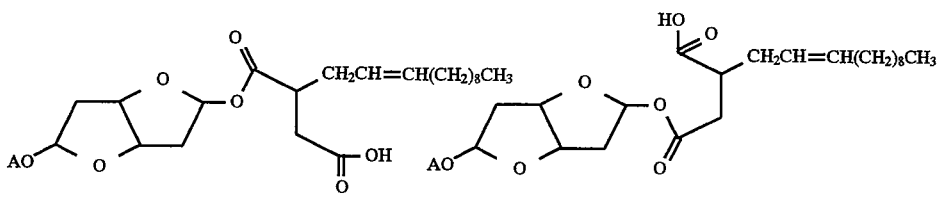
Q = 412.1, When A = H
V = 678.4, When A = C$_{16}$H$_{27}$O$_3$
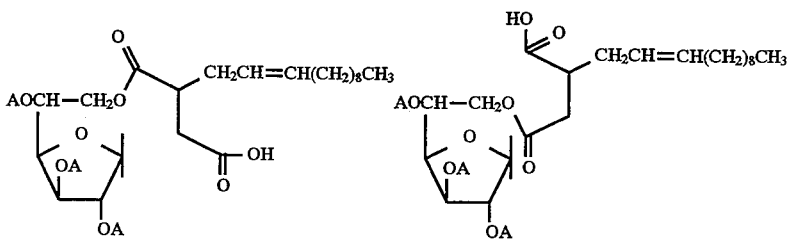
R = 430.1, When A = H
W = 696.4, When A = H or C$_{16}$H$_{27}$O$_3$
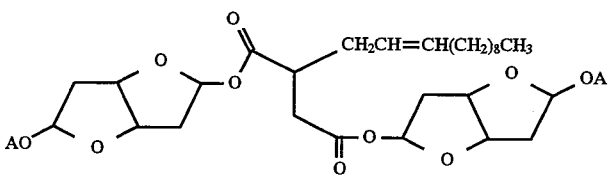
S = 540.2, When A = H
X = 806.0, When A = H or C$_{16}$H$_{27}$O$_3$

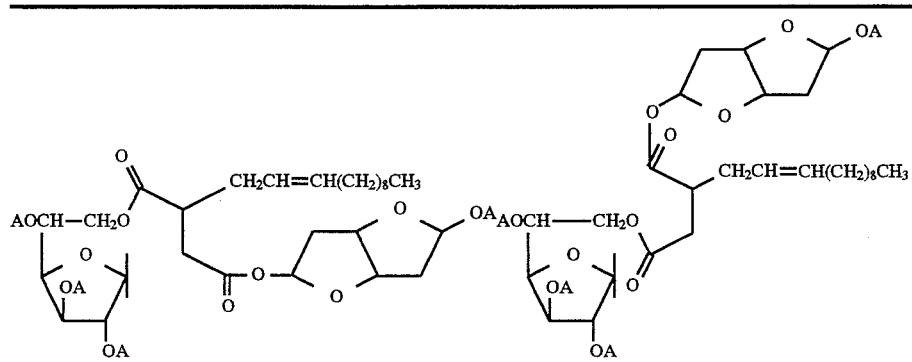

T = 558.3, When A = H
Y = 824.4, When A = H or $C_{16}H_{27}O_3$

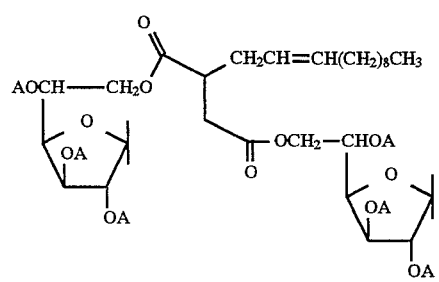

U = 594.2, When A = H
Z = 842.0, When A = H or $C_{16}H_{27}O_3$

Example 2

Preparation of Dodecenyl d-Glucosuccinimide

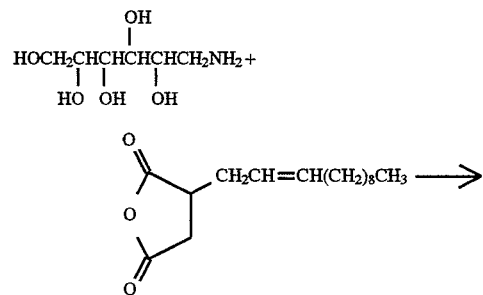

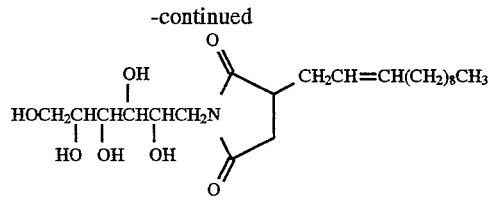

A 100 ml four necked round bottom flask equipped with a mechanical stirrer, thermometer, nitrogen inlet and short path distillation head was charged with recrystallized D-glucamine (14.6 g, $8.06 \times 10^{-2}$ mole, 99.9+% pure), distilled dodecenyl succinic anhydride (21.5 g, $8.06 \times 10^{-2}$ mole) and sodium methoxide (0.07 g, $1.30 \times 10^{-3}$ mole). The reaction mixture was heated to 150° C. for 4 hours under a mild nitrogen blanket giving 34.1 g (98.5% yield) of dodeceyl D-glucosuccinimide as a crystalline solid.

| IR Analysis (cm −1, Nujol) | |
|---|---|
| cm − 1 | Functional Group |
| 3660–3070 | Hydrogen Bonded O — H Stretch |
| 3000–2820 | C — H and =C — H Stretch |
| 1770 and 1700 | C = O Asymmetric and Symmetric Stretch (Imide) |
| 1450 and 1375 | $CH_3$ Bend |
| 1465 | $CH_2$ Bend |
| 1200–1000 | C — O Stretch |
| 980–890 | =C — H Out of Plane Bend |
| 720 | $CH_2$ Rock |

| C13 NMR Analysis (δ, ppm, DMSO D6/TMS) | | |
|---|---|---|
| Estimated C13 Spectrum (δ) | Found (δ) | Carbon # |
| 14.1 | 14.0 | 17 |
| 22.7 | 22.2 | 16 |

-continued

| | | |
|---|---|---|
| 27.3–29.5 | 28.6–29.1 | 14 |
| 30.5 | 31.5 | 11 |
| 32.0 | 32.0 | 15 |
| 35.5 | 33.2 | 8 |
| 39.8 | Under DMSO | 9 |
| 46.1 | 41.7 | 6 |
| 64.9 | 63.4 | 1 |
| 70.9 | 69.3 | 5 |
| 71.9 | 69.9 | 4 |
| 71.9 | 71.6 | 3 |
| 71.9 | 71.9 | 2 |
| 128.6 | 125.4 (Cis) | 13 |
| 128.6 | 125.8 (Trans) | 13 |
| 136.2 | 132.4 (Cis) | 12 |
| 136.2 | 133.5 (Trans) | 12 |
| 173.7 | 176.8 | 10 |
| 174.6 | 179.6 | 7 |

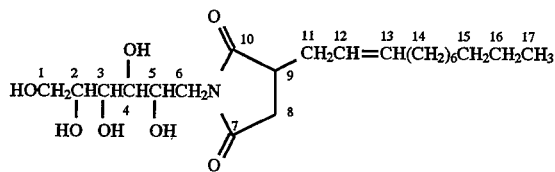

H1 NMR Analysis (δ, ppm, DMSO D6/TMS)

| (δ) | Proton Type |
|---|---|
| 0.9 t | C$\underline{H}_3$ |
| 1.2 s | (C$\underline{H}_2$)$_7$, >C$\underline{H}_2$CH=CH |
| 1.9–2.0 bm | C$\underline{H}_2$N, CH=CHC$\underline{H}_2$(CH$_2$)$_7$ |
| 2.1–2.9 m | Succinate Ring (C$\underline{H}$C$\underline{H}_2$) |
| 3.2–3.7 m | Sugar Protons |
| 3.8–3.9 bm | Sugar Protons |
| 4.3–4.4 m | Sugar Protons |
| 4.5 d | Sugar Protons |
| 4.8 d | Sugar Protons |
| 5.2–5.6 m | C$\underline{H}$=C$\underline{H}$ (Cis and Trans) | s = singlet, d = doublet, t = triplet, m = multiplet and bm = broad multiplet

FAB MS Analysis

| m/e | Compound | Ion |
|---|---|---|
| 358.2 | Dodecenyl D-Glucosuccinimide – 4 H$_2$O | (M + 1 –72)+ |
| 376.2 | Dodecenyl D-Glucosuccinimide – 3 H$_2$O | (M + 1 –54)+ |
| 394.2 | Dodecenyl D-Glucosuccinimide – 2 H$_2$O | (M + 1 –36)+ |
| 412.2 | Dodecenyl D-Glucosuccinimide – 1 H$_2$O | (M + 1 –18)+ |
| 430.2 | Dodecenyl D-Glucosuccinimide + 1 | (M + 1)+ |
| 452.2 | Dodecenyl D-Glucosuccinimide + Na + | (M + 23)+ |
| 593.3 | Dodecenyl D-Bis(gluco)succinamide –1 H$_2$O | (N + 1 – 18)+ |
| 611.3 | Dodecenyl D-Bis(gluco)succinamide + 1 | (N + 1)+ |
| 633.3 | Dodecenyl D-Bis(gluco)succinimide + Na + | (N + 23)+ |
| 718.3 | Didodecenyl D-Glucosuccinimidesuccinate + Na + | (P + 23)+ |

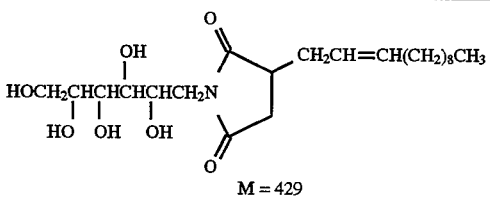

M = 429

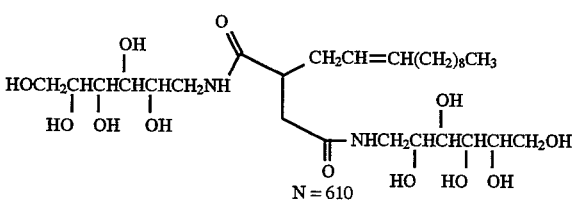

N = 610

-continued

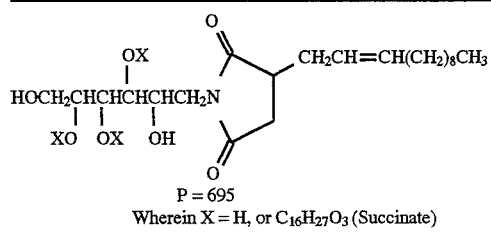

P = 695
Wherein X = H, or $C_{16}H_{27}O_3$ (Succinate)

HPLC Analysis

| Compound | Purity |
|---|---|
| D-Glucamine | 0.22% |
| Didodecenyl D-Glucosuccinimidesuccinate | 1.38% |
| Dodecenyl D-Bis(gluco)succinamide | 2.09% |
| Dodecenyl D-Glucosuccinimide | 96.31% |

Column: Two 4.6 mm×15 cm (Hexyl Regis Columns)
Partical Size: 5 gm
Mobil Phase: 30% Methanol/30% Acetonitrile/40% Water Containing 14.0 g/L Sodium Perchlorate
Detector: Refractive Index Detector
pH=2.1 with Phosphoric Acid
Sample Size: 0.0430 g/25 ml
Flow Rate: 1.4 ml/min
Temperature: 35° C.

Discussion of Examples 1 and 2

As seen in comparative Example 1, prior art methods provide anionic surfactants as a mixture of several different compounds resulting in the production of a thick viscous amber syrup which is difficult to handle and isolate. Whereas the method of the present invention, Example 2, can provide solid nonionic surfactants in good yield, high purity and desirable color without hydroxyl group protection, oligomerization or polymerization. The method of the present invention is a significant improvement over prior art methods.

Example 3

Preparation of Commercial Grade Dodecenyl D-Glucosuccinimide

A 100 ml four necked round bottom flask equipped with a mechanical stirrer, thermometer, nitrogen inlet and short path distillation head was charged with D-glucamine (20.0 g, 0.11 mole), dodecenyl succinic anhydride (29.4 g, 0.11 mole) and sodium methoxide (0.10 g, 1.85 ×10$^{-3}$ mole). The reaction mixture was heated to 150° C. for 6 hours under a mild nitrogen blanket giving 46.0 g (97.0% yield) of dodecenyl D-glucosuccinimide as a crystalline solid.

Example 4

Preparation of Dodecenyl D-Glucosuccinimide in the Presence of a

Reaction Solvent and Recrystallizing Solvent

A 100 ml four necked round bottom flask equipped with a mechanical stirrer, thermometer, nitrogen inlet and condensor is charged with D-glucamine (10.0 g, 5.52×10$^{-2}$ mole) dodecenyl succinic anhydride (14.7 g, 5.52×10$^{-2}$ mole), sodium methoxide (0.05 g, 9.26×10$^{-4}$ mole) and t-butanol (25 ml). The reaction mixture was heated to reflux (108° C.) for several hours and the solvent removed by vacuum distillation (50 mm Hg) to a maximum temperature of 150° C. The reaction mixture was cooled to room temperature and recrystallized from ethyl acetate (100 ml). The product was filtered, washed with cold ethyl acetate (3×20 ml) and dried under vacuum giving 18.4 g (77.6% yield) of dodecenyl D-glucosuccinimide as a crystalline solid.

Example 5

Preparation of Dodecenyl D-Glucosuccinimide in the Presence of a Color

Improvement Agent

A 100 ml four necked round bottom flask equipped with a mechanical stirrer, thermometer, nitrogen inlet and short path distillation head was charged with D-glucamine (20.0 g, 0.11 mole), dodecenyl succinic anhydride (29.4 g, 0.11 mole), sodium borohydride (0.02 g, 5.29×10$^{-4}$ mole) and sodium methoxide (0.05 g, 9.26×10$^{-4}$ mole). The reaction mixture was heated to 145° C. for 6 hours under a mild nitrogen blanket giving 46.3 g (97.7% yield) of dodecenyl D-glucosuccinimide as a crystalline solid.

Example 6

Preparation of Dodecyl D-Glucosuccinimide

A 100 ml four necked round bottom flask equipped with a mechanical stirrer, thermometer, nitrogen inlet and short path distillation head was charged with D-glucamine (10.0 g, 5.52×10$^{-2}$ mole), dodecyl succinic anhydride (14.8 g, 5.52×10$^{-2}$ mole) and sodium methoxide (0.07 g, 1.30×10$^{31}$ 3 mole). The reaction mixture was heated to 170° C. for 6 hours under a mild nitrogen blanket giving 23.6 g (99.1% yield) of dodecyl D-glucosuccinimide as a crystalline solid.

Example 7

Preparation of Tetradecenyl D-Glucosuccinimide

A 100 ml four necked round bottom flask equipped with a mechanical stirrer, thermometer, nitrogen inlet and short path distillation head was charged with D-glucamine (10.6 g, 5.58×10$^{-2}$ mole), tetradecenyl succinic arthydride (17.2 g, 5.58×10$^{-2}$ mole) and sodium methoxide (0.06 g, 1.11×10$^{-3}$ mole). The reaction mixture was heated to 175° C. for 6 hours under a mild nitrogen blanket giving 25.5 g (95.3% yield) of teradecenyl D-glucosuccinimide as a crystalline solid.

Example 8

Preparation of Tetradecyl D-Glucosuccinimide

A 100 ml four necked round bottom flask equipped with a mechanical stirrer, thermometer, nitrogen inlet and short path distillation head was charged with D-glucamine (10.0 g, $5.52 \times 10^{-2}$ mole), tetradecyl succinic anhydride (16.4 g, $5.52 \times 10^{-2}$ mole) and anhydrous potassium carbonate (0.2 g, $1.45 \times 10^{-3}$ mole). The reaction mixture was heated to 185° C. for 7 hours under a mild nitrogen blanket giving 23.7 g (93.4% yield) of tetradecyl D-glucosuccinimide as a crystalline solid.

Example 9

Preparation of Decenyl D-Glucosuccinimide

A 100 ml four necked round bottom flask equipped with a mechanical stirrer, thermometer, nitrogen inlet and short path distillation head was charged with D-glucamine (15.0 g, $8.82 \times 10^{-2}$ mole), decenyl succinic anhydride (19.7 g, $8.82 \times 10^{-2}$ mole) and sodium methoxide (0.08 g, $1.48 \times 10^{-3}$ mole). The reaction mixture was heated to 150° C. for 4 hours under a mild nitrogen blanket giving 32.8 g (98.7% yield) of decenyl D-glucosuccinimide as a crystalline solid.

Example 10

Preparation of Decyl D-Glucosuccinimide

A 100 ml four necked round bottom flask equipped with a mechanical stirrer, thermometer, nitrogen inlet and short path distillation head was charged with D-glucamine (15.0 g, $8.82 \times 10^{-2}$ mole), decyl succinic anhydride (19.9 g, $8.82 \times 10^{-2}$ mole) and sodium methoxide (0.08 g, $1.48 \times 10^{-3}$ mole). The reaction mixture was heated to 150° C. for 5 hours under a mild nitrogen blanket giving 32.6 g (97.6% yield) of decyl D-glucosuccinimide as a crystalline solid.

Example 11

Preparation of Octenyl D-Glucosuccinimide

A 100 ml four necked round bottom flask equipped with a mechanical stirrer, thermometer, nitrogen inlet and short path distillation head was charged with D-glucamine (10.0 g, $5.52 \times 10^{-2}$ mole), octenyl succinic arthydride (11.6 g, $5.52 \times 10^{-2}$ mole) and sodium methoxide (0.05 g, $9.26 \times 10^{-4}$ mole). The reaction mixture was heated to 135° C. for 6 hours under a mild nitrogen blanket giving 20.3 g (98.5% yield) of octenyl D-glucosuccinimide as a crystalline solid.

Example 12

Preparation of Octyl D-Glucosuccinimide in the Presence of a Color Improvement Agent A 100 ml four necked round bottom flask equipped with a mechanical stirrer, thermometer, nitrogen inlet and short path distillation head was charged with D-glucamine (10.0 g, $5.52 \times 10^{-2}$ mole), octyl succinic anhydride (11.7 g, $5.52 \times 10^{-2}$ mole), sodium methoxide (0.05 g, $9.26 \times 10^{-4}$ mole), sodium borohydrate (0.01 g, $2.64 \times 10^{-4}$ mole) and sodium metabisulfite (0.005 g, $2.63 \times 10^{-5}$ mole). The reaction mixture was heated to 140° C. for 6 hours under a mild nitrogen blanket giving 19.9 g (96.0% yield) of octyl D-glucosuccinimide as a crystalline solid.

Example 13

Preparation of Decenyl 6-Imino-6-Deoxy-α-D-Methylglucopyranoside Succinate a.) 6-0-p-Tolylsulfonyl-α-D-Methylglucopyranoside A 100 ml four necked round bottom flask equipped with a mechanical stirrer, thermometer, nitrogen inlet and short path distillation head was charged with methyl a-D-glucopyranoside (6.0 g, $3.09 \times 10^{-2}$ mole) and anhydrous pyridine (55 ml) under a mild nitrogen blanket. The solution was cooled to 0° C. and p-toluenesulfonyl chloride (6.3 g, $3.30 \times 10^{-2}$ mole) dissolved in pyridine (15 ml) was added dropwise. The reaction mixture was allowed to stir at room temperature for about 2 days and the pyridine was removed by vacuum distillation. The resulting residue was dissolved in chloroform (75 ml) and washed with an aqueous solution of potassium hydrogen sulfate and potassium hydrogen carbonate. The chloroform was removed by rotaevporation and the resulting syrup dissolved in toluene (100 ml) at reflux, afterwhich, a precipate formed upon cooling which was filtered, washed with cold toluene (3×25 ml) and dried under vacuum giving 5.6 g (51.9% yield) of 6-O-p-tolylsulfonyl-α-D-methylglucopyranoside with a melting point of 117°–119° C.

b.) 6-Amino-6-Deoxy-α-D-Methylglucopyranoside

A 250 ml two necked round bottom flask equipped with a nitrogen outlet and inlet was charged with a solution of 6-O-p-tolylsulfonyl-α-D-methylglucopyranoside (5.0 g, $1.44 \times 10^{-2}$ mole) dissolved in methanol (180 ml) and cooled to 0° C. The solution was saturated with anhydrous ammonia and charged to an 300 ml autoclave which was heated for 1 day at 120° C. The solution was treated with charcoal, refluxed for 2 hours, filtered over celite and washed with methanol (3×35 ml). The solution was then treated with Amberlite IRA-401S ion-exchange resin, stirred, filtered and the solvent (methanol) removed by rotaevaporation giving 2.5 g (89.9% yield) of 6-amino-6-deoxy-α-D-methylglucopyranoside as a syrup.

c.) Decenyl 6-Imino-6-Deoxy-α-D-Methylglucopyranoside Succinate

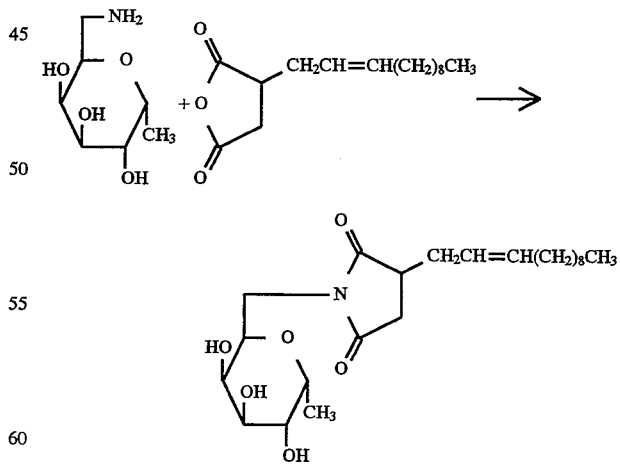

A 25 ml four necked round bottom flask equipped with a mechanical stirrer, thermometer, nitrogen inlet and short path distillation head was charged with 6-amino-6-deoxy-α-D-methylglucopyranoside (2.0 g, $1.04 \times 10^{-2}$ mole), decenyl succinic anhydride (2.5 g, $1.04 \times 10^{-2}$ mole) and sodium methoxide (0.007 g, $1.30 \times 10^{-4}$ mole). The reaction mixture was heated to 135° C. for 6 hours under a mild nitrogen blanket giving 4.4 g (97.8% yield) of decenyl 6-imino-6-deoxy-α-D-methylglucopyranoside succinate.

Example 14

Preparation of Dodecenyl 3-Imino-1,2-Propanediol Succinate

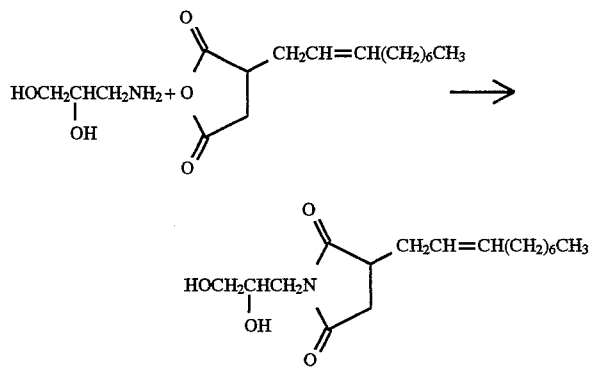

A 100 ml four necked round bottom flask equipped with a mechanical stirrer, thermometer, nitrogen inlet and short path distillation head was charged with 3-amino-1,2-propandiol (8.0 g, $8.78 \times 10^{-2}$ mole), dodecenyl succinic anhydride (23.4 g, $8.78 \times 10^{-2}$ mole) and sodium methoxide (0.05 g, $9.26 \times 10^{-4}$ mole). The reaction mixture was heated to 135° C. for 6 hours under a mild nitrogen blanket giving 28.3 g (94.9% yield) of dodecenyl 3-imino-1,2-propanediol succinate.

Example 15

Preparation of Dodecenyl Monoethanolsuccinimide/Dodecenyl D-Glucosuccinamide

A 100 ml four necked round bottom flask equipped with a mechanical stirrer, thermometer, nitrogen inlet and short path distillation head was charged with monoethanolamine (5.0 g, $8.19 \times 10^{-2}$ mole), D-glucamine (3.7 g, $2.05 \times 10^{-2}$ mole), dodecenyl succinic anhydride (27.3 g, 0.10 mole) and sodium methoxide (0.05 g, $9.26 \times 10^{-4}$ mole). The reaction mixture was heated to 135° C. for 6 hours under a mild nitrogen blanket.

Examples 16–17

The Physical Chemistry of Alkyl- and Alkenyl D-Glycasuccinimides

There are several unique characteristic properties that distinguish surface-active materials (surfactants) from other non-surface active materials. These include critical micelle concentration and surface tension reduction. The following examples will show that the alkyl- and alkenyl D-glyca-succinimides of the invention to be surface-active and are therefore considered to be a new class of sugar based surfactant.

Example 16

Critical Micelle Concentration

The critical micelle concentration (CMC) is defined as the concentration at which a surfactant forms micelles in aqueous solution. Micellization is the preferred interfacial phenomena, since certain surfactant benefits such as foam production depend on the formation of these aggregates in solution. Materials that do not form micelles do not provide any foam.

The CMC value of dodecenyl D-glucosuccinimide was determined by plotting surface tension as a function of log(concentration) and extra-polating linear points to obtain an intersection point. The concentration at this point was taken as the CMC. The technique used was the Wilhelmy plate method and the instrument used was a Lauda Auto-Tensiometer. While wishing not to be bound to theory, it is believed that surfactants with low CMC values form micelles more readily at lower concentrations than those with high CMC values.

The critical micelle concentration (CMC) value of dodecenyl D-glucosuccinimide (molecular weight=447.56 g/mole) was determined and is set forth below:

| The Critical Micelle Concentration of Dodecenyl D-Glucosuccinimide | | | |
|---|---|---|---|
| Entry | Surfactant | CMC | Temperature (°C.) |
| 1 | Dodecenyl D-Glucosuccinimide | 0.12 mM (0.0054%) | 25 |
| 2 | Triton X-100[a] | 0.24 mM (0.0145%) | 25 |
| 3 | Nonidet P-40[b] | 0.29 mM (0.0175%) | 25 |

[a]Triton X-100 is a commercial nonionic surfactant [polyoxyethylene (9.5) p-tert-octyl-phenyl ether] sold by Union Carbide Chemical Company.
[b]Nonidet-P-40 is a commercial nonionic surfactant [polyoxyethylene (9.0) p-tert-octyl-phenyl ether] available through Sigma Chemical Company.

A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential. From the above table, it can be seen that dodecenyl D-glucosuccinimide is properly balanced and forms micelles at a surprising low critical micelle concentration which is comparable to Triton X-100 and Nonidet P-40, two common petrochemically derived nonionic surfactants. This finding suggests that the alkyl- and alkenyl D-glycasuccinimide compounds of the invention are surface-active.

Example 17

Surface Tension Reduction

An important characteristic feature that surfactants have is the tendency for them to absorb at the water/air interface in an oriented manner, thereby altering the interfacial free energy of that surface. The surface free energy per unit area or surface tension (γ), is a measure of this work and may be considered as the minimum amount of work required to bring sufficient surfactant molecules to the surface.

The surface tension (γ) value of dodecenyl D-glucosuccinimide was determined and is set forth below:

| Surface Tension of Dodedcenyl D-Glucosuccinimide at the Water/Air Interface ||||
| Entry | Surfactant | γ | Temperature (°C.) |
| --- | --- | --- | --- |
| 1 | Dodecenyl D-Glucosuccinimide | 29.4 dyn/cm | 25 |
| 2 | Water | 72.0 dyn/cm | 25 |

From the above table it can be seen that dodecenyl D-glucosuccinimide absorbs strongly at the water/air interface resulting in a significant reduction in water surface tension. This finding suggests that the alkyl- and alkenyl D-glycasuccinimide compounds of the invention are surface-active.

Example 18

The Krafft Point of Alkyl- and Alkenyl D-Glycasuccinimides

The temperature at and above which surfactants begin to form micelles instead of precipitates is referred to as the Krafft point (Tk) and at this temperature the solubility of a surfactant becomes equal to its CMC (numerical value at which micelles are formed).

The appearance and development of micelles are important since certain surfactant properties such as foam production depend on the formation of these aggregates in solution.

The Krafft point was measured by preparing 650 ml of a 0.1% dispersion of glycasuccinimide in water by weight. If the surfactant was soluble at room temperature, the solution was slowly cooled to 0° C. If the surfactant did not precipitate out of solution, its Krafft point was considered to be <0° C. (less than zero). If the surfactant precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point. The Krafft point of various alkyl- and alkenyl D-glycasuccinimide compounds are as follows:

| The Krafft Point ($T_k$) of Alkyl- and Alkenyl D-Glucosuccinimides ||
| Compound | $T_k$ (°C.), 0.1% |
| --- | --- |
| Octyl D-Glucosuccinimide | <0° C. |
| Octenyl D-Glucosuccinimide | <0° C. |
| Decyl D-Glucosuccinimide | <0° C. |
| Decenyl D-Glucosuccinimide | <0° C. |
| Dodecyl D-Glucosuccinimide | 28° C. |
| Dodecenyl D-Glucosuccinimide | <5° C. |
| Tetradecyl D-Glucosuccinimide | 33° C. |

From the above table it can be seen that the alkyl- and alkenyl glycasuccinimides of the invention are readily soluble in water and form micelles at low temperatures.

Example 19

The Foam Height of Alkyl- and Alkenyl D-Glycasuccinimides

Since most of the foaming data on surfactants is typically obtained by the Ross-Miles method (Ross, J. and Miles, G. D. Am Soc. for Testing Material Method D1173-63 Philadelphia, PA (1953); Oil & Soap (1958) 62:1260) the foaming ability of these surfactants were acquired using this method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% glycasuccinimide concentration, 40° C. and 0 ppm (parts per million) hardness. The foam height of the of several alkyl- and alkenyl D-glycasuccinimides are as follows:

| The Foam Height (FH) of D-Glucosuccinimides (0 ppm Hardness) |||
| Compound | Initial FH | Final FH(10 Min.) |
| --- | --- | --- |
| Octyl D-Glucosuccinimide | 97 | 85 |
| Octenyl D-Glucosuccinimide | 99 | 86 |
| Decyl D-Glucosuccinimide | 210 | 193 |
| Decenyl D-Glucosuccinimide | 201 | 185 |
| Dodecyl D-Glucosuccinimide | 185 | 173 |
| Dodecenyl D-Glucosuccinimide | 172 | 153 |
| Tetradecyl D-Glucosuccinimide | negligible | negligible |

From the above table it can be seen that the alkyl- and alkenyl glycasuccinimides of the present invention provide a copious stable foam and are therefore surface-active.

Example 20

Preparation of Dodecenyl Dimethylsuccinate

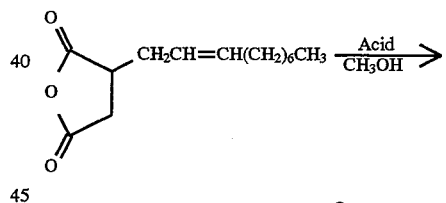

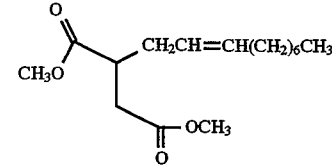

A 250 ml four necked round bottom flask equipped with a mechanical stirrer, thermometer and condenser was charged with dodecenylsuccinic arthydride (15.0 g, 5.63× $10^{-2}$ mole), methanol (135.0 g, 4.21 moles for 10% total solids) and methanesulfonic acid (4 drops). The reaction mixture was heated at reflux for 16 hours, cooled to room temperature, neutralized with 0.1 N sodium methoxide in methanol followed by vacuum distillation giving 16.4 g (99.0% yield, 94.3% purity by GC).

Example 21

Preparation of Dodecyl Dimethylsuccinate

A 250 ml four necked round bottom flask equipped with a mechanical stirrer, thermometer and condenser was charged with dodecylsuccinic anhydride (15.0 g, 5.59×10$^{-2}$ mole), methanol (150.0 g, 4.21 moles for 9.1% total solids) and methanesulfonic acid (4 drops). The reaction mixture was heated at reflux for 24 hours, cooled to room temperature, neutralized with 0.1 N sodium methoxide in methanol followed by vacuum distillation giving 16.4 g (99.0% yield, 98.4% purity by GC)

Example 22

Preparation of Tetradecenyl Dimethylsuccinate

A 250 ml four necked round bottom flask equipped with a mechanical stirrer, thermometer and condenser was charged with tetradecenylsuccinic anhydride (8.6 g, 2.90× 10$^{-2}$ mole), methanol (130.0 g, 4.21 moles for 6.2% total solids) and methanesulfonic acid (3 drops). The reaction mixture was heated at reflux for 16 hours, cool to room temperature and neutralized with 0.1 N sodium methoxide in methanol followed by vacuum distillation giving 9.2 g (98.4% yield, 98.3% purity by GC)

Example 23

Preparation of Dodecenyl Bis(Methyl D-Gluco) succinamide

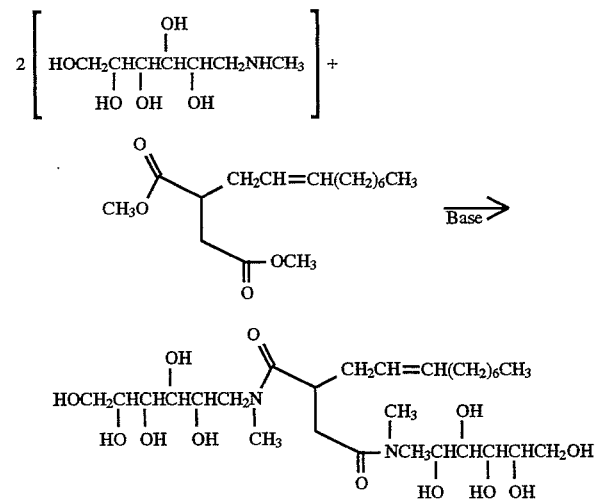

A 100 ml four necked round bottom flask equipped with a mechanical stirrer, thermometer and nitrogen inlet/outlet was charged with methyl D-glucamine (6.6 g, 3.40×10$^{-2}$ mole), dodecenyl dimethylsuccinate (5.0 g, 1.70×10$^{-2}$ mole, Example 20) and sodium methoxide (0.1 g, 1.85×10$^{-2}$ mole). The reaction mixture was heated to 140° C. for 6 hours under a mild nitrogen blanket giving 9.9 g (93.8% yield).

Example 24

Preparation of Dodecyl Bis(D-Gluco)succinamide

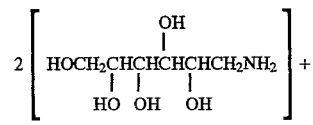

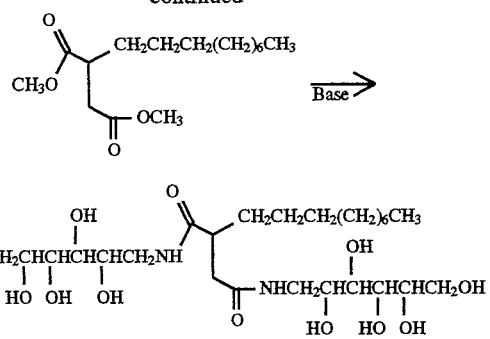

A 50 ml four necked round bottom flask equipped with a mechanical stirrer, thermometer and nitrogen inlet/outlet was charged with D-glucamine (7.5 g, 4.12×10$^{-2}$ mole), dodecyl dimethylsuccinate (6.1 g, 2.06 ×10$^{-2}$ mole, Example 21) and sodium methoxide (0.1 g, 1.85×10$^{-2}$ mole). The reaction mixture was heated to 140° C. for 6 hours under a mild nitrogen blanket giving 11.6 g (94.7% yield).

Example 25

Preparation of Dodecenyl Bis(Glycero)succinamide

[Dodecenyl Bis(3-Amido-1,2-Propandiol) Succinamide]

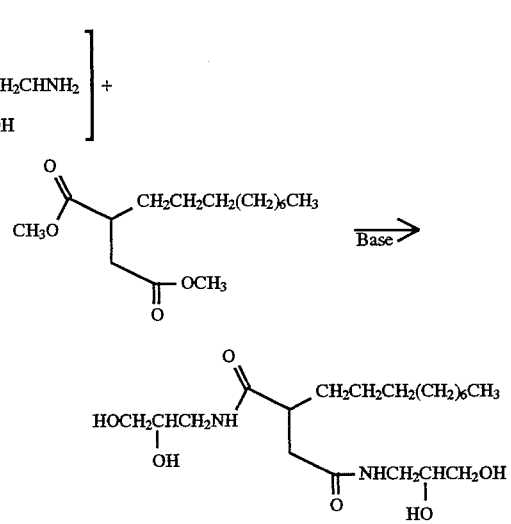

A 50 ml four necked round bottom flask equipped with a mechanical stirrer, thermometer and nitrogen inlet/outlet was charged with 3-amino-1,2-propanediol (3.1 g, 3.40× 10$^{-2}$ mole), dodecenyl dimethylsuccinate (5.0 g, 1.70×10$^{-2}$ mole, Example 20) and sodium methoxide (0.1 g, 1.85×10$^{-2}$ mole). The reaction mixture was heated to 130° C. for 6 hours under a mild nitrogen blanket giving 6.9 g (98.4% yield).

Example 26

Preparation of Tetradecyl Bis(Methyl D-Gluco) succinamide/Tetradecyl

Bis(Monoethanol)succinamide

A 50 ml four necked round bottom flask equipped with a mechanical stirrer, thermometer and nitrogen inlet/outlet was charged with methyl D-glucamine (1.8 g, 9.25×10⁻³ mole), monoethanolamine (1.7 g, 2.77×10⁻² mole), tetradecenyl dimethylsuccinate (6.0 g, 1.85×10⁻² mole) and sodium methoxide (0.1 g, 1.85×10⁻² mole). The reaction mixture was heated to ° C. for 8 hours under a mild nitrogen blanket giving 6.4 g (97.5% yield).

Example 27

Preparation of Dodecenyl Bis(Methyl D-Gluco) succinamide

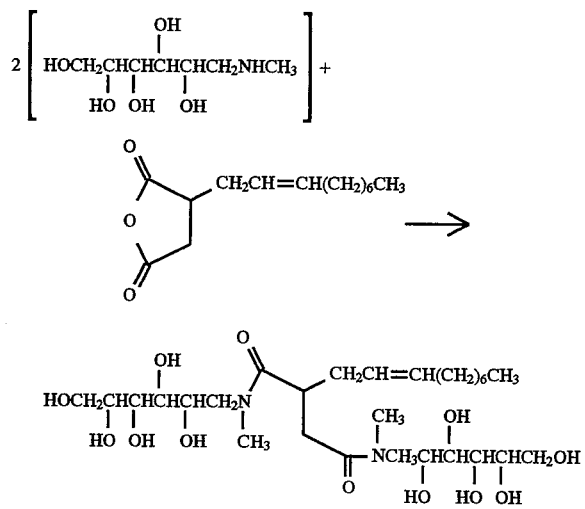

A 100 ml four necked round bottom flask equipped with a mechanical stirrer, thermometer and nitrogen inlet/outlet was charged with dodecenylsuccinic anhydride (9.0 g, 3.38× 10⁻² mole), methanol (50 ml, 1.23 mole) and methanesulfonic acid (4 drops). The reaction mixture was heated under reflux for 6 hours followed by neutralization with sodium methoxide dissolved in methanol (0.1 N). To the mixture was added methyl D-glucamine (13.2 g, 6.76×10⁻² mole) and sodium methoxide catalyst (0.1 g, 1.85×104 mole). The reaction mixture was heated under reflux for 6 hours and methanol removed by simple distillation. The reaction was stirred for at 135° C. for 4 hours giving 19.5 g (92.9% yield)

Example 28

Preparation of Dodecenyl Methyl D-Glucosuccinamide Methyl Succinate

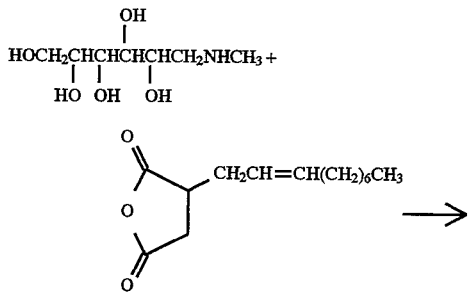

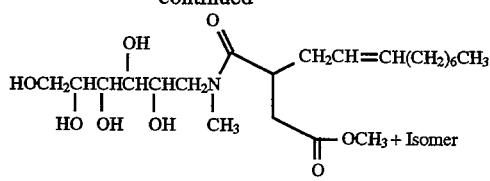

A 100 ml four necked round bottom flask equipped with a mechanical stirrer, thermometer and nitrogen inlet/outlet was charged with dodecenylsuccinic anhydride (9.0 g, 3.38× 10⁻² mole), methanol (50 ml, 1.23 mole) and sulfuric acid (0.1 g). The reaction mixture was heated to 60° C. for 4 hours followed by neutralization with sodium methoxide dissolved in methanol (1 N). The solvent was removed by vacuum distillation. To the reaction mixture was added methyl D-glucamine (6.6 g, 3.38×10⁻² mole) and sodium methoxide catalyst (0.1 g, 1.85×10⁻³ mole). The product was heated at 140° C. for 6 hours followed by neutralization with formic acid. The product was washed with acetone giving 14.5 g (93.3% yield).

Home Application and Use

The nonionic glycasuccinamide and bis(glyca) succinamide surfactants of the present invention are useful in detergent, personal product, oral hygiene, food and pharmacological compositions which are available in a variety of types and forms. Preferred applications are detergent, personal product and oral hygiene compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners shampoos, conditioning shampoos, antidandruff shampoos. antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like.

Examples bath products include, but are not limited to bath oils, foam or bubble bathes, therapeutic bathes, after bath products, after bath splash products and the like.

Examples cleansing products include, but are not limited to shower cleansers, shower gels, body shampoos, hand/ body/facial cleansers, abrasive scrub cleansing products, astringent cleansers, makeup cleansers, liquid soaps, toilet soap bars, syndet bars and the like.

Examples skin care products include, but are not limited to hand body/facial moisturizers, hand/body/facial creams, massage creams, hand/body/facial lotions, sunscreen products, tanning products, self-tanning products, aftersun products, masking products, lipsticks, lip gloss products, rejuvenating products, antiaging products, antiwrinkle products. anti-cellulite products, antiacne products and the like.

Examples shaving products include, but are not limited to shaving creams, aftershave products, preshave products and the like.

Examples deodorant/antiperspirant products include, but are not limited to deodorant products, antiperspirant products and the like.

A classification according to oral hygiene type would consist of, but is not limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

A classification according to detergent, personal product and oral hygiene form would consist of aerosols, liquids, gels, creams, lotions, sprays, pastes, roll-on, stick, tablet, powdered and bar form.

A comprehensive list of essential and optional ingredients that are useful in detergent, personal product and oral hygiene compositions are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

Industrial Application and Use

The glycasuccinamide and bis(glyca)succinamide compounds of the invention are useful as surface-active agents (surfactants).

This invention has been described with respect to certain preferred embodiments and various modifications and variations in the light thereof will be suggested to persons skilled in the art and are to be included within the spirit and purview of this application and the scope of the appended claims. For example, it is known that under certain conditions, D-glucamine and methyl D-glucamine can loose water and cyclize to form sorbitan amine and sorbitan methylamine respectively, which can also react with alkyl and alkenyl succinic anhydrides or their derivatives, to produce sorbitan succinamide surfactants. It is also known, that under certain conditions, methyl D-glucamine can undergo esterfication with alkyl and alkenyl succinic anhydrides or their derivatives, at the hydroxyl group instead of amidation at the methyl amino group to produce ester linked succinate surfactants. These products may be present in low amounts in some cases and generally do not have any serious detrimental effects on the reaction.

What is claimed is:

1. A nonionic alkyl- or alkenyl bis(glyca)succinamide surfactant compound having the formula:

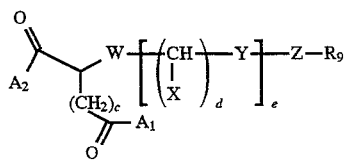
(II)

wherein $A_2$ is selected from the group consisting of the following structures which are attached to the succinate ring via the nitrogen atom on said structures:

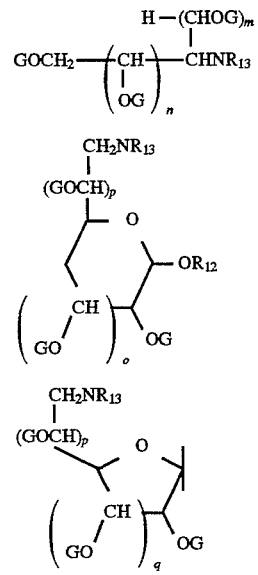

$A_1$ is $A_2$, $OR_{12}$, $N(R_{12})_2$ group or mixtures thereof;

G is hydrogen;

X is hydrogen, an alkyl group having about 1 to about 4 carbon atoms:

Y is an oxygen atom;

Z is a CH=CH, $CH_2CH_2$ group or mixtures thereof;

W is a $CH_2$ group, oxygen atom or mixtures thereof;

$R_9$ is a straight or branched chain saturated hydrocarbon radical having about 4 to about 24 carbon atoms;

$R_{12}$ is hydrogen, an alkyl, alkenyl or hydroxyalkyl group having about 1 to about 4 carbon atoms or mixtures thereof;

$R_{13}$ is hydrogen, a straight or branched chain saturated or unsaturated hydrocarbon which may be unsubstituted or substituted with a hydroxyl, polyhydroxyl radical having about 1 to about 6 carbon atoms;

c=1; d=1–4; e=0–5; m=0; n=1–4; O=0–1; p=0–1; and q=1.

2. A compound according to claim 1 wherein $A_2$ is selected from the group consisting of the following structures which are attached to the succinate ring via the nitrogen atom on said structures:

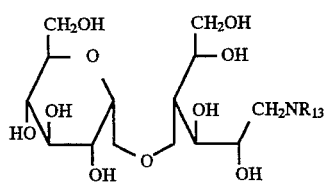

-continued

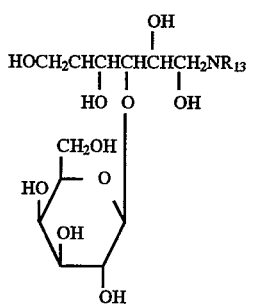

$A_1$ is $A_2$, $OR_{12}$, $N(R_{12})_2$ group or mixtures thereof;

X is hydrogen or an alkyl group having about 1 to about 4 carbon atoms;

Y is an oxygen atom;

Z is a CH=CH, $CH_2CH_2$ group or mixtures thereof;

W is a $CH_2$ group, oxygen atom or mixtures thereof;

$R_9$ is a straight or branched chain saturated hydrocarbon radical having about to about 22 carbon atoms;

$R_{13}$ is hydrogen, a straight or branched chain saturated or unsaturated hydrocarbon which may be unsubstituted or substituted with a hydroxyl, polyhydroxyl radical having about 1 to about 6 carbon atoms;

c=1; d=1–4; and e=0–5.

* * * * *